United States Patent
Dahne et al.

(10) Patent No.: US 12,226,515 B2
(45) Date of Patent: Feb. 18, 2025

(54) METHOD FOR COLOURING HAIR INCLUDING PRETREATMENT

(71) Applicant: WELLA OPERATIONS US, LLC, Calabasas, CA (US)

(72) Inventors: Lars Siegfried Dahne, Berlin (DE); Mandy Hecht, Darmstadt (DE); Mathias Kurt Herrlein, Kronberg (DE); Katrin Kaestle, Ober-Ramstadt (DE); Bryan Patrick Murphy, Loveland, OH (US); Monica Jo Patten, Jeannette, PA (US)

(73) Assignee: WELLA OPERATIONS US, LLC, Calabasas, CA (US)

( * ) Notice: Subject to any disclaimer, the term of this patent is extended or adjusted under 35 U.S.C. 154(b) by 0 days.

(21) Appl. No.: 16/096,191

(22) PCT Filed: Apr. 25, 2017

(86) PCT No.: PCT/US2017/029413
§ 371 (c)(1),
(2) Date: Oct. 24, 2018

(87) PCT Pub. No.: WO2017/189574
PCT Pub. Date: Nov. 2, 2017

(65) Prior Publication Data
US 2019/0143150 A1    May 16, 2019

Related U.S. Application Data

(60) Provisional application No. 62/326,953, filed on Apr. 25, 2016.

(51) Int. Cl.
*A61K 8/22*    (2006.01)
*A61K 8/84*    (2006.01)
(Continued)

(52) U.S. Cl.
CPC .............. *A61K 8/91* (2013.01); *A61K 8/22* (2013.01); *A61K 8/84* (2013.01); *A61Q 5/065* (2013.01);
(Continued)

(58) Field of Classification Search
None
See application file for complete search history.

(56) References Cited

U.S. PATENT DOCUMENTS

| 4,660,580 A | 4/1987 | Hoch et al. | |
| 2003/0154562 A1* | 8/2003 | Sarojini | A61Q 5/10 8/405 |
| 2004/0154108 A1* | 8/2004 | Narasimhan | A61Q 5/10 8/405 |

(Continued)

FOREIGN PATENT DOCUMENTS

| DE | 102012201265 A1 | 8/2013 |
| EP | 2020254 A1 | 2/2009 |

(Continued)

OTHER PUBLICATIONS

"European Application Serial No. 17725380.4, Communication Pursuant to Article 94(3) EPC mailed Dec. 4, 2019", 4 pgs.

(Continued)

*Primary Examiner* — Bethany P Barham
*Assistant Examiner* — Barbara S Frazier
(74) *Attorney, Agent, or Firm* — Dennemeyer & Associates LLC

(57) ABSTRACT

Method for colouring hair comprising pretreating the hair with at least one primer composition before treating the hair with a polymeric hair colouring system.

7 Claims, 3 Drawing Sheets

| Sample | Water | Shampoo |
|---|---|---|
| Cocoamidopropyl Betaine | | |
| Reference Red 4B | | |

(51) Int. Cl.
  *A61K 8/91*    (2006.01)
  *A61Q 5/06*    (2006.01)
  *A61Q 5/10*    (2006.01)
(52) U.S. Cl.
  CPC .......... *A61Q 5/10* (2013.01); *A61K 2800/432* (2013.01); *A61K 2800/4324* (2013.01); *A61K 2800/49* (2013.01); *A61K 2800/542* (2013.01); *A61K 2800/5424* (2013.01); *A61K 2800/5426* (2013.01); *A61K 2800/884* (2013.01)

(56) References Cited

U.S. PATENT DOCUMENTS

2009/0185993 A1* 7/2009 Nocker .................. A61Q 5/065
  424/70.2
2011/0247644 A1* 10/2011 Oberkobusch ........... A61K 8/40
  132/208
2016/0120285 A1* 5/2016 Crne ...................... A45D 19/00
  132/208

FOREIGN PATENT DOCUMENTS

FR          2457306 A1   12/1980
WO     WO-0162221 A1 *   8/2001  ............... A61K 8/19
WO    WO-2017189574 A1   11/2017

OTHER PUBLICATIONS

"European Application Serial No. 17725380.4, Response filed Jun. 3, 2019 to Communication Pursuant to Rules 161(1) and 162 EPC", w/ English Claims, 11 pgs.
"International Application Serial No. PCT US2017 029413, International Preliminary Report on Patentability mailed Nov. 8, 2018", 8 pgs.
"International Application Serial No. PCT/US2017/029413, International Search Report mailed Jul. 13, 2017", 4 pgs.
"International Application Serial No. PCT/US2017/029413, Written Opinion mailed Jul. 13, 2017", 6 pgs.

* cited by examiner

| Sample | Water | Shampoo |
|---|---|---|
| Cocoamidopropyl Betaine | | |
| Reference Red 4B | | |

Figure 1

| Sample | Water | Shampoo |
|---|---|---|
| Hydrogen peroxide | | |
| Reference Red 4B | | |

Figure 2

| Sample | Water | Shampoo |
|---|---|---|
| Bleach | | |
| Reference Red 4B | | |

Figure 3

| Sample | Water | Shampoo |
|---|---|---|
| Ammonium thioglycolate | | |
| Reference Red180 | | |

Figure 4

| Sample | Water | Shampoo |
|---|---|---|
| Sodium hypochlorite | | |
| Reference Red180 | | |

Figure 5

METHOD FOR COLOURING HAIR INCLUDING PRETREATMENT

CROSS-REFERENCE TO RELATED APPLICATION

This application is a U.S. National Stage Filing under 35 U.S.C. 371 from International Application No. PCT/US2017/029413, filed on Apr. 25, 2017, and published as WO 2017/189574 on Nov. 2, 2017, which claims the benefit of priority to United States Provisional Application No.: 62/326,953, filed on Apr. 25, 2016, which application is incorporated by reference herein in its entirety.

FIELD OF THE INVENTION

The invention relates to a method for colouring hair comprising pretreating the hair with at least one primer composition before treating the hair with a polymeric hair colouring system. The hair colouration which is obtained according to the method of the present invention is particularly advantageous in term of colour intensity and stability, root-to-tip evenness as well as enhanced washfastness.

BACKGROUND OF THE INVENTION

Different methods for changing the natural colour of hair are known in the art. These methods involve the use of hair colouring compositions which allow either permanent or temporary change of hair colour.

Hair colouring compositions which are used to permanently change the colour of hair, also called oxidative hair colouring compositions, typically comprise oxidative hair dye precursors, which can diffuse into the hair through the cuticle and into the cortex where they then react with each other and a suitable oxidizing agent to form the end dye molecules. Due to their larger size, the resultant molecules are unable to readily diffuse out of the hair during subsequent washing with water and/or detergents; hence delivering a consumer-desired permanency of colour. This reaction typically takes place at approximately pH 10 to 11 in the presence of an alkalizing agent and an oxidizing agent. Typically an oxidizing composition (also called developer and/or oxidizing component) comprising the oxidizing agent and a dye composition (also called tint or dye component) comprising the alkalizing agent and if present the hair dye precursors are mixed shortly before use. The consumer repeats this process regularly in order to maintain the desired hair colour, shade and intensity of colour and to ensure continual, even coverage of the hair including coverage of new hair growth. The problem with standard oxidative hair colouring methods is that the conditions under which the reaction is taking place, i.e. the high pH value as well as the presence of an oxidizing agent may cause damage to the structure of the hair and may be irritating for the scalp of the user, especially when such a process is repeated regularly and the compositions which are usually used have an undesirable odour. Furthermore, obtaining the desired colour result is not easy since standard oxidative hair colouring compositions are reactive compositions and it is therefore not easy to control the reaction on hair. Finally, once the hair has been coloured with oxidative hair colouring compositions, it is particularly difficult for the user to remove totally the colour or even to a large extent, e.g. to retrieve its natural hair colour. In order to do so, the user would typically need to either colour its hair with a new oxidative hair colouring composition or wait for the new hair to grow.

Alternatively, methods for temporarily changing the colour of hair have also been developed. These methods usually involve the application of hair colouring compositions comprising direct dyes. Direct dye compositions are usually less aggressive for the hair since they are non-reactive compositions. However, since direct dyes are low molecular weight molecules, they may have the tendency to also colour the scalp of the user. Moreover, the hair colouration which is obtained with direct dyes is typically characterized by a weaker washfastness than when the hair is coloured with standard oxidative hair colouring compositions. Specifically, the colouration is typically fading after regular washing of the hair with standard shampoo compositions, and thus, the desired colour intensity remains stable merely for a couple of days.

Methods for temporarily changing the colour of hair involving the application of hair colouring compositions comprising polymeric dyes have also been developed. The hair colouration which is obtained by application of polymeric dyes onto hair is typically characterized by an increased washfastness as compared to direct dyes, but a weaker washfastness as compared to the application of standard oxidative hair colouring compositions. In order to achieve an intensive colouration, a sufficient amount of such polymer dyes has to be deposited onto the user's hair. However, this is only achievable by performing a multitude of colour-layer cycles which is very time intensive, and thus not very user-friendly. Thus, with standard polymeric dye treatments, it may be difficult to achieve an enhanced colour intensity and stability as well as a good washfastness under user-friendly conditions.

Therefore, there is still the need for a method for temporarily changing the colour of hair providing the hair with the desired colour result and colour intensity in an easy manner. There is also the need for a method for temporarily changing the colour of hair providing a hair colouration which is characterized by a better stability and good washfastness as compared to methods using direct dyes. Furthermore, there is also the need for a method for temporarily changing the colour of hair involving the use of hair colouring compositions which do not colour the user's scalp and achieve a more intense coloration with shorter application time.

SUMMARY OF THE INVENTION

The present invention relates to a method for colouring hair comprising: carrying out the following sequence of steps:
  a) pretreating a first portion of the hair with at least one primer composition to modify the surface of the hair,
  b) optionally repeating step a) at least once;
  c) treating a second portion of the hair with a hair colouring system comprising at least one cationic polymer and/or at least one anionic polymer,
wherein the first and second portions of the hair have at least one common area.

The present invention also relates to a hair colouration obtainable by the method as defined herein, and to a kit for treating hair, preferably comprising a first compartment comprising the primer composition as defined herein and a second compartment comprising the hair colouring system as defined herein.

BRIEF DESCRIPTION OF THE DRAWINGS

FIGS. 1-5 illustrate a comparison between hair swatches coloured with and without pretreatment and washed after being coloured with water/shampoo.

DETAILED DESCRIPTION OF THE INVENTION

As used herein the term "hair" to be treated may be "living" i.e. on a living body or may be "non-living" i.e. in a wig, hairpiece or other aggregation of non-living keratinous fibres. Mammalian, preferably human hair is preferred. However wool, fur and other keratin containing fibres are suitable substrates for the compositions according to the present invention.

All ratios or percentages are weight ratios or weight percentages unless specifically stated otherwise.

By "hair colouring system" it is meant any system, formulation, article, product which is suitable for changing the colour result and/or colour intensity of hair.

By "multilayer structure" it is meant that at least two polymeric layers are placed on hair on top of each other by alternating the deposition of a first polymeric layer and a second polymeric layer, thereby forming a layer-by-layer structure.

By "an area of hair" it is meant at least a portion of hair including only a small portion of one single hair up to the complete hair of head.

By "cationic polymer" it is meant any polymer comprising an overall charge at full protonation which is positive.

By "coloured cationic polymer" it is meant any cationic polymer comprising at least one chromophore and/or at least one fluorophore either in the skeleton or as pendent group.

By "uncoloured cationic polymer" it is meant any cationic polymer which does not comprise any chromophore or fluorophore either in the skeleton or as pendent group.

By "polymeric backbone" it is meant any series of covalently bound atoms that together create the continuous chain of a molecule, including the main chain and all other pendant chains.

By "homopolymer" it is meant any polymer that contains only a single type of repeat unit.

By "heteropolymer" it is meant any polymer that contains a mixture of at least two different repeat units.

As used herein the expression "labelling degree k" is a measure for the loading of a polymer with a dye. The "labelling degree k" is defined as n:m, with n being the number of chromophores and/or fluorophores per polymer and m being the monomeric units per polymer.

A "higher labelling degree" means more chromophore and/or fluorophore molecules per polymer. For example, a labelling degree 1:20 is higher than a labelling degree 1:100. A "lower labelling degree" means less chromophore and/or fluorophore molecules per polymer. For example, a labelling degree 1:30 is lower than a labelling degree 1:5.

By "anionic polymer" it is meant any polymer comprising an overall charge at full deprotonation which is negative.

By "coloured anionic polymer" it is meant any anionic polymer comprising at least one chromophore and/or at least one fluorophore either in the skeleton or as pendent group.

By "uncoloured anionic polymer" it is meant any anionic polymer which does not comprise any chromophore or fluorophore either in the skeleton or as pendent group.

By "full protonation" it is meant the state at which the different protonable groups of a polymer are all fully protonated.

By "full deprotonation" it is meant the state at which the different deprotonable groups of a polymer are all fully deprotonated.

By "linked to the polymer" it is meant a covalent bond between the chromophore and/or the fluorophore with the polymer.

By "type of chromophore and/or fluorophore" it is meant whether the chromophore and/or of the fluorophore is cationic, anionic, non-ionic, or amphoteric.

Method for Colouring Hair

Embodiments of the present invention relate to a method for colouring hair. The method comprises step a) of pretreating a first portion of the hair with at least one primer composition to modify the surface of the hair.

To modify the surface of the hair by the pretreatment of step a) means that the surface of the first portion of the hair before pretreatment with the primer composition has a different structure and/or different properties than the surface of the first portion of the hair after pretreatment. The surface structure of the latter may differ in various features from the structure of the former.

In principle, the surface of human hair shows structures of hydrocarbon, hydroxyl, primary amide, and basic amino acid and disulfide functions on its surface. Hydrophobic interactions play a strong role in the reactivity of hair toward cosmetics due to frequent occurrence of hydrocarbon-bearing amino acids. A primer composition applied upon pretreatment to the hair can serve as an "activating agent" of the hair surface and converts the native hair surface from a hydrophobic entity with low surface charge to a more hydrophilic, thus to a more polar, and/or to a more negatively charged surface.

For instance, considering only the overall charge of the hair surface, the hair surface of the first portion before pretreatment may have a particular overall negative charge while the hair surface of the first portion after pretreatment may have an overall negative charge which is greater (i.e. more negative) than the overall negative charge before pretreatment. In principle, such a surface modification can be considered as a "physical" modification of the hair surface.

In addition or alternatively, pretreatment may change the morphology of the hair surface. For instance, the cuticle of the first portion of the hair may be modified such that small interstices are formed between at least some of the hair cell shingles. In these interstices, the polymer layers from step c) may be trapped, thereby improving the adherence of the first polymer layer deposited on the hair surface. Such a surface modification can also be considered as a "physical" modification of the hair surface.

In addition or alternatively, modifying the surface of the hair may also mean that the chemical properties of the hair surface are modified. Such a surface modification can be considered as a "chemical" modification of the hair surface.

For instance, upon "chemical" modification, at least some of the proteins of the exocuticle and/or the endocuticle can be oxidized or reduced, thereby resulting in a different protein structure in the respective areas. Such a modified protein structure may again contribute to the overall surface charge of the hair surface. Moreover, reductive primer compositions produce a higher cysteic acid content, partial removal of hair lipids and the formation of Bunte salts on the fiber surface. On the other hand, oxidative primer compositions also remove the hydrophobic surface barrier, create acidic sulfur compounds (sulfonate groups, mercaptanes, sulfinates etc.) on the fiber surface, and further provide an acidic, hydrophilic hair surface. Accordingly, upon chemical modification, the hair surface becomes more hydrophilic and more acidic or anionic in character and removes hair products or environmental soils from the surface at the same time. From that starting point, the overall charge of the hair can be tailored and the extent of deposition of a cationic polymer (provided in step c) by electrostatic binding can be increased. Thus, the subsequent treatment with an oppositely charged polymer partner results in a complex that is more resistant to removal by water, shampoo, or mechanical forces.

Further, modifying the chemical properties of the hair surface may also include modifying the tertiary structure of the exocuticle and/or the endocuticle proteins, thereby resulting in an increased amount of possible anchoring positions for the polymers which can be deposited thereon in the subsequent method step c).

Accordingly, modifying the surface of the hair may include one of the foregoing modifications, or any combination thereof, resulting in an "activation" of the hair surface. The above exemplified surface modifications caused by the pretreatment of step a) are of course non-exhaustive.

By activating the hair surface of the first portion as discussed above, the following beneficial effects are achieved:

- It is possible to bind a maximum amount of (coloured and/or uncoloured) polymers to the hair surface, e.g., due to the increase of the overall negative charge of the hair surface and/or due to the increase of anchoring positions on the hair surface. This enables performing a reduced number of colour-layer cycles for achieving the same or even a greater colour intensity, thereby decreasing the overall time necessary for the desired hair colouring.
- It is possible to increase the grade of adherence (adhesion strength) of each of the (coloured and/or uncoloured) polymers to the hair surface of the first portion of the hair, e.g., due to the increase of the overall negative charge of the hair surface and/or due to the increase of anchoring positions on the hair surface. This leads to e.g., an improved washfastness and colour stability.
- It is further possible to adjust the morphological and/or chemical and/or overall charge of different hair portions to each other. Such "different" hair portions may include e.g., different areas on the head of hair (e.g., hair at the temples vs. fringe), or may include different areas on a single hair. For instance, hair roots may have different surface properties than hair tips, e.g., due to physiological and/or environmental impacts. By performing the pretreatment of the present invention, these properties may be adjusted to each other, thereby providing a hair surface with—from the root to the tip—substantially equal surface properties. By applying the polymeric hair colouring system thereto, it is possible to achieve a substantially homogenous multi-layer structure resulting in a substantially even colour intensity over the whole hair portion. Accordingly, an even hair surface can be restored and the attraction of the coloured polymer to the hair can be enhanced in order to achieve intense colouration with short application time and greater evenness.

The method can further comprise step b) of repeating step a) at least once. In step b), step a) may be repeated at least twice, alternatively at least three times. Alternatively, in step b), step a) may be repeated from 1 to 3 times. Performing the pretreatment step more than once may ensure that the hair surface is sufficiently modified in the sense as described before depending on the condition of the user's hair surface right before pretreatment. The condition of the user's hair surface in turn depends on various factors, such as age, gender, care, recently applied hair products etc. For instance, when pretreating exhausted hair—be it e.g., through lack of care or too intensive treatment with hair products—it may be advantageous to perform step a) at least twice, preferably three times, in order to achieve the desired hair surface activation as explained hereinbefore.

In a particular aspect, step a) may comprise pretreating the first portion of the hair with a first primer composition, and step b) may comprise pretreating the first portion of the hair with a second primer composition which is different from the first primer composition. Particularly the first primer composition may comprise at least one anionic surfactant as described herein while the second primer composition may comprise any one of the primer compositions as described herein under the provision that the second primer composition does not comprise an anionic surfactant. In a further particular aspect, the first primer composition comprising the at least one anionic surfactant may be substantially free of cationic polymers and/or cationic surfactants. For instance, the first primer composition may be completely free of both cationic polymers and cationic surfactants. Alternatively, the first primer composition may comprise a total concentration of both a cationic polymer and cationic surfactant of <0.1 g/L, alternatively <0.05 g/L, alternatively <0.01 g/L.

The method can further comprise step c) of treating a second portion of the hair with a hair colouring system. The first portion of step a) and the second portion of step b) can have at least one common area. The hair colouring system used in step c) can comprise at least one cationic polymer and/or at least one anionic polymer. Having at least one common area between the first portion of the hair to which the primer composition is applied and the second portion of the hair to which the hair colouring system is applied ensures that at least a portion of the hair colouring system is applied to the same portion of the hair as at least a portion of the primer composition.

The hair colouring system is preferably applied to the hair after the primer composition has been applied to the hair for at least one time. For instance, the primer composition can be applied 1, 2, 3, 4, 5, 6, or 7 times to the first portion of the hair, and in the subsequent step, the hair colouring system can be applied to a second portion of hair wherein the first and the second portions have at least one common area. Having at least one common area between the first portion of the hair to which the primer composition is applied and the second portion of the hair to which the hair colouring system is applied ensures that at least a portion of the hair colouring system is applied to the same portion of the hair as at least a portion of the primer composition.

Applying the hair colouring system to a second portion of hair (i.e. step c)) can comprise the sub-steps of
c1) carrying out the following sequence of steps:
 i) applying a first composition comprising the cationic polymer to a third portion of the hair; and optionally
 ii) applying a second composition comprising at least one anionic polymer to a fourth portion of the hair.

The third and fourth portions of the hair have the second portion of the hair as common area. This means that the overlap between the third portion of the hair and the fourth portion of the hair is defined as the second portion of the hair. This ensures that at least a portion of the second composition is applied to the same portion of the hair as at least a portion of the first composition. This further ensures that at least a portion of the common area of the first and second compositions is applied to the same portion of the hair as at least a portion of the primer composition.

The method may further comprises the optional step c2) of repeating step c1) at least once, wherein the common area of each of the repeated steps c1) of the optional step c2) has at least one common area with the common area of the first and second portions, and the common area of each of the other repeated steps c1) in optional step c2), in case step c2) is repeated more than once. This ensures that at least a portion of each of the primer composition and the hair colouring system which are applied to the hair in each of the sequences of steps is applied to the same portion of the hair.

Each of the first compositions of step c1) and of the repeated steps c1) of step c2) may be the same or different. Each of the second compositions of step c1) and of the repeated steps c1) of step c2) may be the same or different.

According to an embodiment, in step c1) and/or in at least one of the repeated steps c1) of step c2), the cationic polymer is a cationic coloured polymer.

According to an embodiment, in step c1) and/or in at least one of the repeated steps c1) of step c2), the anionic polymer is an anionic coloured polymer.

According to an embodiment, in step c1) and/or in at least one of the repeated steps c1) of step c2), the cationic polymer is a cationic uncoloured polymer.

According to an embodiment, in step c1) and/or in at least one of the repeated steps c1) of step c2), the anionic polymer is an anionic uncoloured polymer.

According to an embodiment, the cationic polymer of step c1) may be uncoloured and the cationic polymer on a repeated step c1) of step c2) may be coloured.

According to an embodiment, the cationic polymer of step c1) may be coloured and the anionic polymer of step c1) may be uncoloured.

In step c1) and/or in each of the repeated step c1) of step c2), the first and the second compositions may be applied all over the hair.

In step c2), step c1) may be repeated at least at least twice, alternatively at least three times. Alternatively, in step c2), step c1) may be repeated from 1 to 3 times.

The method according to the present invention is particularly advantageous. For instance, the method comprising performing the specific pretreatment step in advance to the step of colouring the hair with a polymeric hair colouring system is particularly suitable for providing enhanced colour intensity, even on dark shades, as well as improved colour stability to cosmetic treatments and mechanical abrasion as compared to non-pretreated hair. Moreover, upon pretreatment, root-to-tip variations can be compensated in order to achieve an even coloration of hair without damaging the hair. Further, by pretreating the hair, the washfastness is substantially improved due to a better adherence of the polymeric hair colouring system on the hair. Also, consumers can achieve a more intense colouration by a shorter application time due to a reduced number of colour-layer cycles. This leads to a more user-friendly colouring method.

Specifically, by performing step a) of pretreating a first portion of the hair with at least one primer composition may help to tailor the colour result obtained on different areas of hair, e.g., on the fringe vs. the rest of the head of hair and/or different portions of the hair, e.g., hair roots vs. hair tips. For instance, pretreating only the fringe with the primer composition and subsequently applying the first and second compositions to the whole head of hair (including the fringe) may lead to a different colour intensity in the fringe area vs. the rest of the head of hair. Depending on the grade of overall charge of different hair portions, the polymers subsequently deposited on the hair by performing step c) may attach more or less easily to the hair and therefore a different colour result may be obtained on different portions of the hair which are differently charged. In other instances, an even colour intensity throughout the complete head of hair will be highly desirable. In these cases, it is generally preferred to perform step a) on the complete head of hair.

By performing step c), it is possible to provide the hair with the desired colour result and colour intensity in an easy manner. The method is unique in that in each of the sequence of steps with step c), a second composition comprising at least one anionic polymer is applied to the hair after a first composition comprising at least one cationic polymer has been applied to the hair.

Since the cationic polymers and the anionic polymers which are comprised in respectively the first composition and the second composition are high molecular weight molecules, they usually do not diffuse into the hair or at least only to a limited extent when compared with dyes used in standard oxidative hair colouring methods. They usually form polymeric layers on hair which are placed on top of each other by alternating the deposition of the cationic polymers and the anionic polymers. By performing the sequence of steps i) and ii) of step c1) more than once it is possible to obtain more than two polymeric layers on hair and therefore to have a better control on the final colour result and colour intensity which is obtained. By increasing the number of layers which are applied to the hair it is possible to obtain hair colorations having increased colour intensity. The user may decide on how many times the sequence of steps should be repeated and therefore have a better control over the colour result which is obtained on hair.

Furthermore, it is particularly advantageous to apply a second composition comprising at least one anionic polymer to hair after having applied a first composition comprising at least one cationic coloured polymer. Indeed, the polymer which is comprised in the second composition is negatively charged and therefore the outer layer of the coated hair has an electrostatic structure which is similar to the one of the outer layer of natural hair. Therefore it is possible to apply standard cationic conditioners to the hair after the hair colouring process.

It is particularly important for the method according to the present invention to have an anionic polymeric layer which is positioned on top of the cationic polymeric layer. Indeed, the presence of the anionic layer is essential in order to have the possibility of applying a subsequent cationic layer on top of it when the sequence of steps of the method is carried out more than once. While not wishing to be bound by theory it is also believed that in some embodiments, the anionic polymeric layer may act as a protective layer for the cationic coloured layer which is placed underneath and therefore may contribute to the good washfastness of the hair coloration.

Furthermore, the compositions which are used in the method according to the present invention are particularly advantageous since contrary to standard oxidative hair colouring compositions, these compositions are typically odourless.

In the embodiments wherein in step c2) of the method, step c1) is repeated once, the first composition of step c1) may comprise at least one cationic coloured polymer and the first composition of the repeated step c1) may comprise at least one cationic uncoloured polymer. In the embodiments wherein in step c2) of the method, step c1) is repeated once, the first composition of step c1) may comprise at least one cationic uncoloured polymer and the first composition of the repeated step c1) may comprise at least one cationic coloured polymer.

The method may further comprise step c3) of applying after step c1) a third composition comprising at least one cationic polymer to a fifth portion of the hair wherein the fifth portion of the hair has at least one common area with the common area of step c1).

Alternatively, the method may further comprise the step c4) of applying after step c2) a third composition comprising at least one cationic polymer to a fifth portion of the hair, wherein the fifth portion of the hair has at least one common area with the common area of step c2).

In the steps c3) and/or c4), the third composition may be applied all over the hair. The cationic polymer comprised in the third composition may be a coloured cationic polymer or an uncoloured cationic polymer.

By having a cationic polymeric layer on top of the anionic layer it is possible to provide the user with a good hair feeling which is similar to what is obtained when standard commercially available conditioners are applied to the hair.

Steps a) to c) of the method may further comprise the subsequent sub-step of removing the excess of respectively the primer composition and/or the hair colouring system from the hair. Removing the excess of respectively the primer composition and/or the hair colouring system from the hair may comprise washing and/or rinsing the hair in the respective portions, preferably with a liquid comprising a cosmetically acceptable solvent, more preferably with water.

Steps a) to c) of the method may further comprise the subsequent sub-step of applying energy to the hair in the form of heat, ultrasounds, infrared and/or microwaves. This sub-step may be carried out either after the application of the primer composition or the hair colouring system to the hair or after removing the excess of the primer composition or the hair colouring system from the hair. While not wishing to be bound by theory, it is believed that applying energy to the hair may accelerate the speed of formation of the polymeric layers on the hair and therefore may increase the stability of the layers once they are formed on the hair. The hair may be heated to a temperature ranging from 5° C. to 70° C., alternatively 20° C. to 60° C., alternatively 40° C. to 60° C.

After carrying out the method according to the present invention, a conditioning agent may be applied to the hair. Any of the conditioning agents disclosed hereinafter may be applied to the hair.

The method of the invention is particularly suitable for providing a multilayer structure on an area of hair.

In its smallest version, the multilayer structure merely consists of two polymeric layers, the first polymeric layer being placed on top of the outer layer of natural hair, the second polymeric layer being placed on top of the first polymeric layer. More specifically, the cationic polymer of the first composition is capable of binding to the negatively charged outer layer of the natural hair via ionic linkage. Accordingly, the anionic layer of the second composition is capable of binding to the coloured cationic polymer via ionic linkage. Thereby, a bilayer on hair is formed consisting of a cationic polymer layer covering the outer hair layer followed by an anionic layer covering the coloured cationic polymer layer. Of course, in its smallest version, the cationic and/or the anionic polymers are coloured polymers. That is, at least one of the cationic and anionic polymers comprises a chromophore and or a fluorophore as defined herein.

The multilayer structure is not only restricted to the above-described bilayer structure. In fact, the multilayer structure can comprise x cationic polymer layers and y anionic layers in alternating sequence, with x and y, independent from each other, being 1, 2, 3, 4, 5, 6, 7, 8, 9 or 10, under the provision that at least one of the cationic and anionic polymer layers comprise a chromophore and/or a fluorophore as defined herein. In "alternating sequence" means that two layers of the same ionic type typically do not lie next to each other. For instance, the multilayer structure can comprise two cationic polymer layers and two anionic layers in alternating sequence. The multilayer structure can also comprise three cationic polymer layers and three anionic layers in alternating sequence. Alternatively, the multilayer structure can comprise four cationic polymer layers and four anionic layers in alternating sequence. The total number of polymeric layers with the multilayer structure may be even or odd. For instance, the multilayer structure can comprise two cationic polymer layers and only one anionic layer in alternating sequence, thereby providing the outer layer of the coated hair with a cationic structure. Alternatively, the multilayer structure can comprise three cationic polymer layers and two anionic layer in alternating sequence. A cationic structure of the outer layer can provide the user with a good hair feeling which is similar to what is obtained when standard commercially available conditioners are applied to the hair.

The advantageous multilayer structure can be achieved by performing step c) as defined herein until the desired multilayer structure is obtained.

Since the cationic polymer(s) and the polymer(s) of the multilayer structure are high molecular weight molecules, they usually do not diffuse into the hair or at least only to a limited extent when compared with dyes used in standard oxidative hair colouring methods for permanent change of hair colour. Moreover, they do not colour the scalp of the user, as direct dyes usually do.

Controlling the number of cationic and anionic polymeric layers within the multilayer structure enables a better control on the final colour result and colour intensity by the user. By increasing the number of layers which are applied to the hair it is possible to obtain hair colorations having increased colour intensity. The user may decide on how many times the sequence of steps should be repeated and therefore have a better control over the colour result which is obtained on hair. The user may further decide on which parts of the hair of head have greater/weaker colour intensity than other parts.

Furthermore, in case the anionic polymer which is comprised in the second composition is the outer layer of the multilayer structure, an electrostatic structure is provided which is similar to the one of the outer layer of natural hair, i.e. a negatively charged surface. Therefore it is possible to apply standard cationic conditioners to the hair after the hair colouring process.

The presence of the anionic layer is further essential in order to have the possibility of applying a subsequent cationic layer on top of it when a multilayer of more than two polymeric layers is desired. While not wishing to be bound by theory it is also believed that in some embodiments, the anionic polymeric layer may act as a protective layer for the coloured cationic layer which is placed underneath and therefore may contribute to the good washfastness of the hair coloration. Contrary thereto, when using direct dyes, the hair colouration which is obtained is typically characterized by a weaker washfastness, especially when the hair is washed with standard shampoo compositions.

Furthermore, the compositions which are used in the hair colouring system according to the present invention are particularly advantageous since—contrary to standard oxidative hair colouring compositions—these compositions are typically odourless.

As such, the hair colouration which is obtained by the method of the invention is particularly advantageous in terms of washfastness, stability and tailoring of the colour result. Specifically, based on the identity of chromophores and/or fluorophores attached to the cationic polymer, and particularly based on the degree to which the cationic polymer is labelled (i.e. the labelling degree), the user can achieve colours from pastel to intense, without hair damage. These coloured complexes show enhanced stability to cosmetic treatments and mechanical abrasion compared to the cationic polymer alone on hair.

These advantageous effects are unique since current hair colouring methods require deposition of the colour inside the hair to achieve any type of lastingness, particularly resistance to mechanical removal, shampoo fading and water bleed. However, such a deposition on the hair surface leads to a coated feel, and this coating is removed easily by mechanical abrasion.

Most attempts at surface colouring of hair fibres with coloured polymers have relied on exploitation of the negative surface charge on hair, particularly by attaching cationic chromophores to a polymer to enhance the attraction of the coloured polymer to hair. However, this results in over- or under-deposition of the colour depending on the level of surface charge of the hair, driven by fibre damage from previous cosmetic treatments and environmental factors.

With the method of the invention, the opportunity is given to tailor the colour effects and intensity. By performing the pretreatment step as well as by the specific choice of various chromophores and/or fluorophores (anionic, cationic, amphoteric, or non-ionic) and their specific distribution (i.e. the specific labelling degree) on the cationic polymer of the hair colouring system, it is possible to avoid the above described problems and to deliver colours ranging from pastels to intense.

In the step c) described herein, the chromophores and/or fluorophores are covalently linked to a cationic polymer having e.g. primary amines that binds electrostatically to the hair surface. The extent of deposition in a single treatment is driven by the nascent charge of the cationic polymer at the pH of the hair surface, which is a function of damage. From that starting point, the overall charge of the coloured cationic polymer can be tailored by firstly choosing specific chromophores and/or fluorophores that are anionic, non-ionic, amphoteric, or cationic (depending on the desired colour, behaviour in wet atmosphere etc.), and by secondly choosing the ideal labelling degree for these specific chromophores and/or fluorophores. Subsequent treatments with an oppositely charged polymer partner (i.e. an anionic polymer), results in a complex that is more resistant to removal by water, shampoo, or mechanical forces.

With current technologies, when a chromophore is attached to a polymer, it is inherently more difficult to get pastel or light shades that are even. Using a lower concentration of the coloured polymer, as one possibly would for a monomeric dye formulation, can lead to patchy or uneven colour, because the polymer will first seek the more highly charged areas of the hair. By tailoring specific concentrations of the chromophores and/or fluorophores on the polymer backbone, even colours of all intensities are possible. This is best accomplished by the system according to embodiments using cationic polymers labelled with dyes (i.e. chromophores/and or fluorophores) that result in a balanced interaction with the fibres and that can be prepared reproducibly at a specific labelling degree from very dilute to exhaustive labelling, depending on the type of dyes used. Finally, the ability to tailor the colour intensity of the polymer gives users (i.e. colourists and consumers) the ability to generate currently impossible colour effects by application of differently coloured layers individually without the drawback of e.g., obtaining over-deposition of colour or colour build-up.

The method of the present invention may particularly enable controlling the colour intensity of hair. Controlling the colour intensity of hair may be particularly achieved by at least one of
- chemically and/or physically modifying (i.e. activating) the hair surface by pretreating the hair with the specific primer composition,
- adjusting the labelling degree of the coloured cationic polymer,
- adjusting the pH value of the first and/or second compositions,
- adjusting the polymer concentrations in the first and/or second compositions,
- adjusting the salt concentration in the first and/or second compositions,
- adjusting the ionic strength in the first and/or second compositions,
- adding specific additives to the first and second compositions, such as additives selected from the group consisting of alkalizing agents, pH modifiers and/or buffering agents, thickeners and/or rheology modifiers, (anionic, cationic, nonionic, amphoteric or zwitterionic) surfactants, and any combination thereof.

Primer Composition

The primer composition of the present invention is used for pretreating the hair to modify the hair surface as explained hereinbefore and may be a chemical primer composition and/or a physical primer composition. A chemical primer composition is understood to chemically modify the surface of the hair as described hereinbefore. Accordingly, a physical primer composition is understood to physically modify the surface of the hair described hereinbefore.

The primer composition may be substantially free of polymers. According to an embodiment, the primer composition may be substantially free of cationic polymers while anionic polymers may be included. According to an embodiment, the primer composition may be substantially free of anionic polymers while cationic polymers may be included. According to an embodiment, the primer composition may be substantially free of both cationic polymers and anionic polymers. For instance, the primer composition may be completely free of polymers, or may comprise a total concentration of polymers <0.1 g/L, alternatively <0.05 g/L, alternatively <0.01 g/L. Preferably, the primer composition does not comprise any of the cationic and/or anionic polymers as defined herein for the first and second compositions of the hair colouring system. Particularly, the primer composition is substantially free of cationic polymers.

In an alternative embodiment, the primer composition may comprise at least one polymer, such as an uncoloured cationic polymer and/or an uncoloured anionic polymer. Suitable uncoloured cationic polymers and uncoloured anionic polymers include those described herein under headlines "cationic polymers" and "anionic polymers".

The primer composition may be substantially free of dyes. For instance, the primer composition may be completely free of dyes, or may comprise a total concentration of dyes <0.1 g/L, alternatively <0.05 g/L, alternatively <0.01 g/L. In this context, a "dye" is understood to be a compound (including a polymer compound) having at least one chromophore and/or fluorophore.

In an embodiment, the primer composition of the present invention may comprise at least one of:
an oxidizing agent, such as a peroxide,
a reducing agent,
a pH≥9,
a salt, such as a cosmetically acceptable salt,
a surfactant,
an oil,
an organic acid,
and any combinations thereof.

According to an embodiment the primer composition comprises a surfactant, particularly an amphoteric surfactant. The primer composition comprising a surfactant such as an amphoteric surfactant may additionally comprise at least one of a salt such as a cosmetically acceptable salt, and an organic acid.

According to an embodiment the primer composition comprises an oxidizing agent such as a peroxide. The primer composition comprising an oxidizing agent such as a peroxide may additionally comprise at least one of a salt such as a cosmetically acceptable salt, and an organic acid. The primer composition comprising an oxidizing agent such as a peroxide may additionally comprise a surfactant selected from cationic surfactants, anionic surfactants, non-ionic surfactants, and amphoteric surfactants as described herein.

According to an embodiment the primer composition comprises a reducing agent. The primer composition comprising a reducing agent may additionally comprise at least one of a salt such as a cosmetically acceptable salt, and an organic acid. The primer composition comprising a reducing agent may additionally comprise a surfactant selected from cationic surfactants, anionic surfactants, non-ionic surfactants, and amphoteric surfactants.

Oxidizing Agents

The primer composition of the present invention may comprise at least one oxidizing agent and/or at least one source of an oxidizing agent. The oxidizing agents may be provided in aqueous solution or as a powder which is dissolved prior to use. Preferred oxidizing agents are water-soluble peroxygen oxidizing agents. As used herein, "water-soluble" means that in standard conditions at least 0.1 g, preferably about 1 g, more preferably 10 g of the oxidizing agent can be dissolved in 1 liter of deionized water at 25° C. Suitable water-soluble oxidizing agents include, but are not limited to: inorganic peroxygen materials capable of yielding hydrogen peroxide in an aqueous solution.

The oxidizing agents are valuable for the initial solubilisation and decolourisation of the melanin (bleaching) as well as for the activation of the hair surface such that through oxidization of proteins located at the hair surface, the overall negative charge is increased. An increased overall negative charge of the hair surface is desirable for a better attachment of the cationic polymer comprised in the hair colouring system applied to the hair in the subsequent step c) of the method of the present invention.

The primer composition may comprise a total amount of oxidizing agents ranging from 0.1% to 12%, alternatively from 0.2% to 12%, alternatively from 0.3%/o to 12%, alternatively from 0.1% to 7%, alternatively from 0.2% to 7%, alternatively from 0.3% to 7%, alternatively from 1% to 7%, alternatively from 0.1% to 5%, alternatively from 0.2% to 50%, alternatively from 0.3% to 5%, alternatively from 0.5% to 5%, alternatively from 1% to 5%, alternatively from 2% to 5%, by total weight of the primer composition. Alternatively, the primer composition may comprise a total amount of oxidizing agents of less than 3%, alternatively less than 2%, alternatively less than 1%, alternatively less than 0.5%, alternatively less than 0.3% alternatively less than 0.1% by total weight of the primer composition. The lower limit for the oxidizing agents may be at least 0.01% by total weight of the primer composition. The primer composition having a low amount of oxidizing agents is less damaging the hair than standard hair colouring composition which usually comprise a high concentration of oxidizing agent.

The primer composition may also be substantially free of oxidizing agents, i.e. having oxidizing agents less than 0.1%, and more particularly less than 0.01% by total weight of the primer composition. For example, a primer composition having surfactants such as amphoteric surfactants may be substantially free of oxidizing agents. A primer composition which comprises oxidizing agents, however, may also include surfactants such as at least one of anionic surfactants, cationic surfactants, amphoteric surfactants, non-ionic surfactants, and combination thereof.

Suitable water-soluble peroxygen oxidizing agents include, but are not limited to: hydrogen peroxide; inorganic alkali metal peroxides (such as sodium periodate and sodium peroxide); organic peroxides (such as urea peroxide and melamine peroxide); inorganic perhydrate salt bleaching compounds (such as the alkali metal salts of perborates, percarbonates, perphosphates, persilicates, persulphates and the like); and mixtures thereof. Inorganic perhydrate salts may be incorporated for example as monohydrates, tetrahydrates. Alkyl/aryl peroxides and/or peroxidases may also be used. Mixtures of two or more such oxidizing agents can be used if desired.

The primer composition may comprise a water-soluble oxidizing agent selected from the group consisting of peroxides, percarbonates (which may be used to provide a source of both oxidizing agent and carbonate ions and or ammonium ions), persulphates, and mixtures thereof. The particularly preferred oxidizing agent is hydrogen peroxide.

When the primer composition of the present invention is obtained by mixing a developer composition and a tint composition prior to use, the oxidizing agent may be present in the developer composition. The developer composition may be based on any desired formulation chassis, including any commercial product, for example an oil-in-water emulsion. Typical developer compositions comprise about 6% or about 90% of the $H_2O_2$ relative to the total weight of the developer composition. A preferred example of a developer composition with respectively about 6% and about 9% $H_2O_2$, comprises as INCI ingredients: Water, $H_2O_2$, Cetearyl Alcohol, Ceteareth-25, Salicylic Acid, Phosphoric Acid, Disodium Phosphate, Etidronic Acid. Another preferred example a developer composition comprises as INCI ingredients: Water, $H_2O_2$, cetearyl alcohol, lanolin alcohol, sodium lauryl sulfate, parfum, salicylic acid, phosphoric acid, disodium phosphate, linalool, hexyl cinnamal, etidronic acid, tocopherol. Another preferred example a developer composition comprises as INCI ingredients: Water, $H_2O_2$, cetearyl alchohol, lanolin alcohol, sodium lauryl sulfate, parfum, salicylic acid, phosphoric acid, disodium phosphate, linalool, hexyl cinnamal, etidronic acid, tocopherol.

Reducing Agents

The primer composition of the present invention may comprise at least one reducing agent and/or at least one source of a reducing agent. The reducing agents may be provided in aqueous solution or as a powder which is dissolved prior to use. The primer composition may comprise a total amount of reducing agents ranging from 0.1% to 15%, alternatively from 0.2% to 12%, alternatively from 0.3% to 12%, alternatively from 0.1% to 7%, alternatively from 0.2% to 7%, alternatively from 0.3% to 7%, alternatively from 1% to 7%, alternatively from 0.1% to 5%, alternatively from 0.2% to 5%, alternatively from 0.3% to 5%, alternatively from 0.5% to 5%, alternatively from 1% to 5%, alternatively from 2% to 5%, by total weight of the primer composition. Suitable reducing agents are Thioglycolic acid, Mercaptanes, Ammonium thioglycolate, Sodium thioglycolate Cysteine, Sodium Sulfite, Ascorbic acid, Glyceryl monothiopropionate. Ammonium thiolactate, Dithiothreitol, Dithioerythritol, Glutathione, Dihydrolipoic acid, 1,3-Dithiopropanol, Thioglycolamide, Glyceryl monothioglycolate, Sodium bisulfite, Sodium hydrogensulfite, Sodiumthiosulfate, Glyceryl thiolactate, and combinations thereof.

The primer composition may also be substantially free of reducing agents, i.e. having reducing agents less than 0.1%, and more particularly less than 0.01% by total weight of the primer composition. For example, a primer composition having surfactants such as amphoteric surfactants may be substantially free of reducing agents. A primer composition which comprises reducing agents, however, may also include surfactants such as at least one of anionic surfactants, cationic surfactants, amphoteric surfactants, non-ionic surfactants, and combination thereof.

The reducing agent(s) may preferably be selected from the group consisting inorganic reducing agent(s) and organic reducing agent(s), and combinations thereof.

Inorganic Reducing Agents:
sulfide, disulfite, thiosulfate, sulfite, phosphonic acid, hydrazine, borohydride, aluminiumhydride, hydrogen, sodium sulfite, sodium bisulfite, sodium hydrogensulfite, sodiumthiosulfate, and combinations thereof.

Organic Reducing Agents:
formic acid, ketoglutarate, DTT red, NADH/H+, dihydrolipoic acid, cysteine, vitamin C, vitamin E, Dithiothreitol (DTT), mercaptanes, thioglycolic acid, ammonium thioglycolate, sodium thioglycolate cysteine, ascorbic acid, glyceryl monothiopropionate, ammonium thiolactate, dithioerythritol, glutathione, 1,3-dithiopropanol, thioglycolamide, glyceryl monothioglycolate, glyceryl thiolactate, and combinations thereof.

The primer composition may include either reducing agent(s) or oxidizing agent(s).

Alternatively, the primer composition may also be substantially free of reducing agents, i.e. having reducing agents less than 0.1%, and more particularly less than 0.01% by total weight of the primer composition. For example, a primer composition having surfactants such as amphoteric surfactants may be substantially free of reducing agents. A primer composition which comprises reducing agents, however, may also include surfactants such as at least one of anionic surfactants, cationic surfactants, amphoteric surfactants, non-ionic surfactants, and combination thereof.

Preferred reducing agents are thioglycolic acid, mercaptanes, ammonium thioglycolate, sodium thioglycolate cysteine, sodium sulfite, ascorbic acid, glyceryl monothiopropionate, ammonium thiolactate, dithiothreitol, dithioerythritol, glutathione, dihydrolipoic acid, 1,3-dithiopropanol, thioglycolamide, glyceryl monothioglycolate, sodium bisulfite, sodium hydrogensulfite, sodiumthiosulfate, glyceryl thiolactate, and combinations thereof.

pH Value

The primer composition of the present invention may have a pH ranging from 7 to 12, alternatively from 8 to 11, alternatively from 9 to 10. Alternatively, the primer composition may have a pH$\geq$9.

The primer composition having an alkaline pH value (preferably pH$\geq$9) is particular advantageous. In principle, the higher the pH of the primer composition, the better the deprotonation of the proteins located at the hair surface, and thus the higher the overall negative charge of the hair surface. A higher overall negative charge of the hair surface is desirable for a better attachment of the cationic polymer comprised in the hair colouring system applied to the hair in the subsequent step c) of the method of the present invention. However, too extreme pH values, e.g., pH>12 may cause damage to the structure of the hair and may be irritating for the scalp of the user, especially when such a process is repeated more than once.

Nevertheless, one of the advantages of the method according to the present invention is that—upon pretreatment—the hair may be coloured with a sufficient colour intensity even if the primer composition has a lower pH. Taking further into account the skin's natural pH levels being in the weakly acid, depending e.g. on the gender and age of the user, the pH levels of the first and second compositions can particularly be tailored for the user's need.

Salt Such as a Cosmetically Acceptable Salt

The primer composition of the present invention may comprise at least one salt, such as a cosmetically acceptable salt. Suitable total concentrations for the cosmetically acceptable salt in the primer composition range from 0 to 1.5 mol/L, alternatively from 0.05 to 1 mol/L, alternatively from 0.2 to 0.5 mol/L.

The cosmetically acceptable salt may be selected from the group consisting of an organic salt, a mineral salt and mixture thereof. The organic salt may be sodium citrate. The mineral salt may be selected from the group consisting of sodium chloride, ammonium sulfate, magnesium chloride, calcium chloride and mixtures thereof. In a preferred embodiment, the cosmetically acceptable salt may be sodium chloride.

Using a cosmetically acceptable salt in the primer composition is another important parameter. For instance, using defined concentrations of cosmetically acceptable salts in the primer composition (e.g. up to 1.5 mol/L) has the effect that the hair surface is saturated with positively charged ions (e.g. sodium ions) and negatively charged ions (i.e. chloride ions). While most of the positively charged ions will stick to the negatively charged hair surface, the negatively charged ions can—after performing step c) of the method of the present invention—gather around the cationic polymer comprised in the hair colouring system as defined herein. The resulting decrease of positive charge in the immediate surroundings of each cationic polymer has the effect that only those parts of the cationic polymer chain which have still enough positive charge will ionically bind to the negatively charged hair surface. Notably, the "stronger" cationic polymers can easily replace the "weaker" salt cations. The number decrease of anchoring sites of each polymer chain results in an undulated orientation of each cationic polymer on the hair surface, thereby enabling the binding of a greater number of cationic polymers. The greater the number of bound cationic polymers on a defined hair surface portion, the more intensive the colour of this portion in case the cationic polymer bears a chromophore and/or a fluorophore. Thus, adjusting the salt concentration in the primer composition may be particularly useful to modify the colour intensity.

Surfactant

The primer composition of the present invention may further comprise at least one surfactant. Surfactants generally have a lipophilic chain which is hydrophobic, with an ionic group (sometimes polar group), which is hydrophilic. Depending on their ionic (or non-ionic) character, surfactants can help adjusting the ionic strength of the primer compositions which may affect the resultant viscosity and root adhesion properties of the primer composition. Furthermore, the amount of adsorbed cationic polymers onto hair from solutions can be influenced by surfactants. Interactions can involve binding of surfactant molecules or involve a perturbation of aggregation or micellization of the surfactant by the presence of the polymer. Additionally hydrophobic forces may act between surfactant molecules adsorbed on different polymer chains. Particularly amphoteric surfactants do not neutralize the charge of the cationic polymer as effectively as anionic surfactants. Thus, cationic polymers (of the subsequently applied hair colouring system) demonstrate a higher affinity for keratins in an amphoteric surfactant system compared to an anionic surfactant system.

Suitable surfactants may have a lipophilic chain length of from about 8 to about 30 carbon atoms.

Typically, the primer composition may comprise a total amount of surfactants ranging from 1% to 60%, alternatively from 2% to 30%, alternatively from 8% to 25%, alternatively from 10% to 20%, by total weight of the primer composition.

Suitable surfactants can be selected from anionic surfactants, cationic surfactants, nonionic surfactants, amphoteric surfactants, and mixtures thereof.

Anionic Surfactant

The primer composition may comprise one or more anionic surfactant(s). The anionic surfactant(s) may preferably comprise one or more linear or branched group(s) comprising at least 8 carbon atoms. The anionic surfactant(s) may more preferably comprise one or more linear or branched group(s) comprising from 8 to 22 carbon atoms. The anionic surfactant(s) may even more preferably comprise one or more linear or branched group(s) comprising from 10 to 22 carbon atoms. The anionic surfactant(s) may most preferably comprise one or more linear or branched group(s) comprising from 16 to 22 carbon atoms. The linear or branched group(s) may optionally comprise at least one heteroatom selected from oxygen, nitrogen, sulfur and halogens. The linear or branched groups may be aliphatic groups.

Suitable anionic surfactant(s) may comprise at least one anionic functional groups at their head selected from sulfate, sulfonate, phosphate and carboxylates.

Suitable alkyl sulfates include ammonium lauryl sulfate, sodium lauryl sulfate (sodium dodecyl sulfate, SLS, or SDS), and alkyl-ether sulfates, such as sodium laureth sulfate (sodium lauryl ether sulfate or SLES), and sodium myreth sulfate.

Further suitable anionic surfactants may include Docusate (dioctyl sodium sulfosuccinate), alkyl-aryl ether phosphate, alkyl ether phosphate, alkyl carboxylate, such as sodium stearate, sodium lauroyl sarcosinate, ammonium laureth sulfate, disodium lauryl sulfosuccinate, and sodium lauryl sulphoacetate.

Preferred anionic surfactants are selected from the group consisting of sodium laurylethersulfate, sodium laurethersulfate, sodium dodecyl sulfate, ammonium laurethethersulfat, ammonium dodecyl sulfate, alkylbenzenesulfonate, and combinations thereof.

Cationic Surfactant

The primer composition may comprise one or more cationic surfactant(s). The cationic surfactant(s) may preferably comprise one or more linear or branched group(s) comprising at least 8 carbon atoms. The cationic surfactant(s) may more preferably comprise one or more linear or branched group(s) comprising from 8 to 22 carbon atoms. The cationic surfactant(s) may even more preferably comprise one or more linear or branched group(s) comprising from 10 to 22 carbon atoms. The cationic surfactant(s) may most preferably comprise one or more linear or branched group(s) comprising from 16 to 22 carbon atoms. The linear or branched group(s) may optionally comprise at least one heteroatom selected from oxygen, nitrogen, sulfur and halogens. The linear or branched groups may be aliphatic groups.

The cationic surfactant(s) may be selected from the group consisting of quaternary ammonium salts, amido-amines, primary amines, secondary amines, tertiary amines and mixtures thereof.

The cationic surfactant(s) may be selected from quaternary ammonium salts having the following formula:

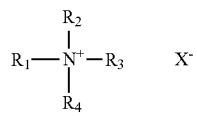

wherein:
  R1 is selected from the group consisting of linear or branched groups optionally comprising at least one heteroatom selected from oxygen, nitrogen, sulfur and halogens, wherein the linear or branched groups comprise from 6 to 22 carbon atoms, preferably from 16 to 22 carbon atoms; and
  R2 is selected from the group consisting of linear or branched groups optionally comprising at least one heteroatom selected from oxygen, nitrogen, sulfur and halogens, wherein the linear or branched groups comprise from 1 to 22 carbon atoms, preferably from 16 to 22 carbon atoms, aryl groups and alkylaryl groups; and
  R3 and R4 are independently selected from the group consisting of linear or branched groups comprising from 1 to 4 carbon atoms, aryl groups and alkylaryl groups; and
  X— is an anion selected from chloride, bromide, iodide, alkyl sulfates, phosphates, alkyl sulfonates, alkylaryl sulfonates and anions derived from organic acids or amino acids.

The linear or branched groups may be aliphatic groups. The aliphatic groups may be selected from alkyl, alkoxy and alkylamide groups.

The amino acid may be glutamic acid. The anions derived from organic acids may be acetate anions or lactates anions.

The cationic surfactant(s) may be selected from amido-amines having the following formula:

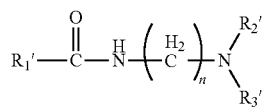

wherein:
  R1' is selected from the group consisting of linear or branched groups optionally comprising at least one heteroatom selected from oxygen, nitrogen, sulfur and halogens, wherein the linear or branched groups comprise from 10 to 22 carbon atoms, preferably from 16 to 22 carbon atoms;

R'2 and R'3 are independently selected from the group consisting of hydrogen, linear or branched groups optionally comprising at least one heteroatom selected from oxygen, nitrogen, sulfur and halogens, wherein the linear or branched groups comprise from 1 to 4 carbon atoms, aryl groups and alkylaryl groups;

n is integer ranging from 1 to 4.

The linear or branched groups may be aliphatic groups. The aliphatic groups may be selected from alkyl, alkoxy and alkylamide groups.

The cationic surfactant(s) may be selected from the group consisting of cetrimonium halide, stearimonium halide, behentrimonium halide, behentrimonium halide, stearamidopropyltrimonium halide, dodecyltrimethylammonium halide, didodecyldimethylammonium halide, tetradecyltrimethylammonium halide, distearyldimethylammonium halide, dicetyldimethylammonium halide, distearoylethyl dimonium halide, behenamidopropyltrimonium methosulfate, behenamidopropyl dimethylamine, stearamidopropyl dimethylamine, behenamidopropyl diethylamine, behenamidoethyl diethylamine, behenamidoethyl dimethylamine, arachidamidopropyl dimethylamine, arachidamidopropyl diethylamine, arachidamidoethyl diethylamine, arachidamidoethyl dimethylamine, and mixtures thereof, wherein the halide is selected from bromide and chloride. The cationic surfactant(s) may preferably be selected from the group consisting of dodecyltrimethylammonium halide, didodecyldimethylammonium halide, tetradecyltrimethylammonium halide, cetrimonium halide and mixtures thereof, wherein the halide is selected from bromide and chloride.

The primer composition comprises a total amount of cationic surfactants ranging from 0.01% to 10%, preferably from 0.05% to 5%, more preferably from 0.3% to 3% by total weight of the primer composition. The amount of each particular cationic surfactant or mixtures thereof described hereinbefore can account for up to 100% (or 100%) of the total amount of cationic surfactants in the primer composition.

Nonionic Surfactant

The primer composition may comprise one or more nonionic surfactant(s). The nonionic surfactant(s) may preferably comprise one or more linear or branched group(s) comprising at least 8 carbon atoms. The nonionic surfactant(s) may more preferably comprise one or more linear or branched group(s) comprising from 8 to 22 carbon atoms. The nonionic surfactant(s) may even more preferably comprise one or more linear or branched group(s) comprising from 10 to 22 carbon atoms. The nonionic surfactant(s) may most preferably comprise one or more linear or branched group(s) comprising from 16 to 22 carbon atoms. The linear or branched group(s) may optionally comprise at least one heteroatom selected from oxygen, nitrogen, sulfur and halogens. The linear or branched groups may be aliphatic groups.

The nonionic surfactants may be selected form the group consisting of alcohols, ethers, esthers, alkanolamides and aminoxides.

Suitable alcohols may include primary alcohols ranging from 8 to 18 carbon atoms. Preferred primary alcohols are fatty alcohols, cetyl alcohol, stearyl alcohol, cetostearyl alcohol (consisting predominantly of cetyl and stearyl alcohols), and oleyl alcohol.

Suitable ethers may include Polyoxyethylene glycol alkyl ethers (Brij) (CH3-(CH2)10-16-(O—C2H4)1-25-OH), Octaethylene glycol monododecyl ether, Pentaethylene glycol monododecyl ether, Polyoxypropylene glycol alkyl ethers (CH3-(CH2)10-16-(O—C3H6)1-25-OH), Glucoside alkyl ethers (CH3-(CH2)10-16-(O-Glucoside) 1-3-OH), Decyl glucoside, Lauryl glucoside, Octyl glucoside, Polyoxyethylene glycol octylphenol ethers (C8H17-(C6H4)-(O—C2H4)1-25-OH, Triton X-100), Polyoxyethylene glycol alkylphenol ethers (C9H19-(C6H4)-(O—C2H4)1-25-OH, Nonoxynol-9), and block copolymers of polyethylene glycol and polypropylene glycol (Poloxamers).

Suitable esthers may include Glycerol alkyl esters, such as Glyceryl laurate, Polyoxyethylene glycol sorbitan alkyl esters, such as Polysorbate, and Sorbitan alkyl esters, such as Spans.

Suitable alkanolamides may include cocamide MEA, cocamide DEA.

Suitable aminoxides may include Dodecyldimethylamine oxide and Polyethoxylated tallow amine (POEA).

Amphoteric Surfactant

The primer composition may comprise one or more amphoteric surfactant(s). The amphoteric surfactant(s) may preferably comprise one or more linear or branched group(s) comprising at least 8 carbon atoms. The amphoteric surfactant(s) may more preferably comprise one or more linear or branched group(s) comprising from 8 to 40 carbon atoms. The amphoteric surfactant(s) may even more preferably comprise one or more linear or branched group(s) comprising from 10 to 40 carbon atoms. The amphoteric surfactant(s) may most preferably comprise one or more linear or branched group(s) comprising from 16 to 35 carbon atoms. The linear or branched group(s) may optionally comprise at least one heteroatom selected from oxygen, nitrogen, sulfur and halogens. The linear or branched groups may be aliphatic groups. Without being bound to theory, it is assumed that the positive portion of the amphoteric surfactant will bind to hair will the negative portion will bind to the cationic polymer provided in the subsequent step c) of the present invention. In other words: the amphoteric surfactant may act as a linker between the hair surface and the cationic polymer, thereby increasing the grade of adherence (adhesion strength) of the first (coloured and/or uncoloured) cationic polymer layer to the hair surface.

Amphoteric (zwitterionic) surfactants have both cationic and anionic centers attached to the same molecule. The cationic part may be based on primary, secondary, tertiary amines or quaternary ammonium cations. The anionic part can be more variable and may include sulfonates, as in the sultaines CHAPS (3-[(3-Cholamidopropyl)dimethylammonio]-1-propanesulfonate) and cocamidopropyl hydroxysultaine.

Suitable amphoteric surfactants may include betaines, such as cocamidopropyl betaine, phospholipids, such as phosphatidylserine, phosphatidylethanolamine, phosphatidylcholine, and sphingomyelins.

Suitable betaines may have the following formula

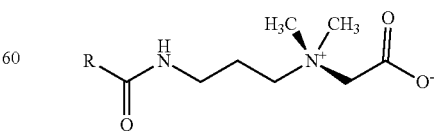

with R=alkyl chain with 5 to 21 C atoms.

Further suitable amphoteric surfactants may include sultaines which may have the following formula

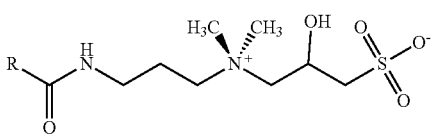

with R=alkyl chain with 5 to 21 C atoms.

Further suitable amphoteric surfactants may include taurin (2-aminoethansulfonic acid), cocoamidopropyl hydroxysultain, N-coco 3-aminopropionic acid, (or the sodium salt thereof), N-tallow 3-iminodipropionate (or the disodium salt thereof), N-carboxymethyl N-dimethyl N-9 octadecenyl ammonium hydroxide, N-cocoamidethyl N-hydroxyethylglycine, cocoamphocarboxyglycinate, cocamidopropyl betaine, and sulfobetaine.

Most preferred amphoteric surfactants are selected from the group consisting of betain, sultaines, phospholipids, aminopropionates, aminoglycinates, amphoacetate, amphodiacetate, amphopropionate, amphohydroxypropylsulfonates, and combinations thereof. Most preferred are betains selected from the group consisting of Cocamidopropyl betaine, Laurylamidopropyl betaine Tetradecyl betaine, Alkylaminopropyl betaine, Octyl betain, Cetyl betain, Staeryl betain.

Further suitable amphoteric surfactants may comprise amino acids. Specifically, amino acids with their polyampholytic character in the primer composition can help to enhance the ionic and hydrophobic interactions between the hair surface. Suitable amino acids may be selected from the group consisting of alanine, arginine, asparagine, aspartic acid, cysteine, glutamic acid, glutamine, glycine, proline, selenocysteine, serine, tyrosine, histidine, isoleucine, leucine, lysine, methionine, phenylalanine, threonine, tryptophan, valine, and combinations thereof.

Oil

The primer compositions of the present invention may comprise at least one oil including oil derived materials.

Typically, the primer composition may comprise a total amount of oils ranging from 1% to 60%, alternatively from 2%/o to 30%, alternatively from 8% to 25%, alternatively from 10% to 20%, by total weight of the primer composition.

Suitable Oils are e.g. Silicone Oils.

Organic Acid

The primer compositions of the present invention may comprise at least one organic acid. Organic acids in the primer composition can help to activate the hair surface by oxidation or reductive processes.

Typically, the primer composition may comprise a total amount of organic acids ranging from 1% to 60%, alternatively from 2% to 30%, alternatively from 8% to 25%, alternatively from 10% to 20%, by total weight of the primer composition. Suitable organic acids are selected from the group consisting of Acetylsalicylic acid, Lactic acid, Glycolic acid, Ferulic acid, and combinations thereof.

Ionic Strength

The primer compositions of the present invention may have an ionic strength as defined herein of less than about 1.35 mole/kg, alternatively from about 0.10 to about 0.75 mole/kg, alternatively from about 0.20 to about 0.60 mole/kg. Whilst not being bound by theory, it is believed that the ionic strength value may also affect the resultant viscosity and root adhesion properties of the primer composition. Therefore, a well-balanced ionic strength as defined above may contribute to an increased interaction between the primer composition and the hair surface resulting in a better "activation" of the hair surface. The ionic strength can be affected by salt resources such as sodium sulphate, ammonium carbonate anti-oxidants and chelants such as EDDS, as well as surfactants.

The ionic strength of the composition is a function of the concentration of all ions present in that solution and is determined according to the formula:

$$I = \frac{1}{2}\sum_{i=1}^{n} m_i z_i^2$$

where $m_i$=molality of ion i (M=mol-/Kg $H_2O$), $z_i$=charge number of that ion, and the sum is taken over all ions in the solution. For example, for a 1:1 electrolyte such as sodium chloride, the ionic strength is equal to the concentration, but for $MgSO_4$ the ionic strength is four times higher. Generally multivalent ions contribute strongly to the ionic strength.

For example the ionic strength of a mixed 0.050 M $Na_2SO_4$ and 0.020 M NaCl solution is: $I=\frac{1}{2}((2\times(+1)^2\times 0.050)+(+1)^2\times 0.020+(-2)^2\times 0.050+(-1)^2\times 0.020)=0.17M$.

Solvents

The primer composition used to carry out step a) of the method according the present invention may further comprise a solvent. The solvent may be selected from water, or a mixture of water and at least one organic solvent to dissolve the compounds that would not typically be sufficiently soluble in water. The primer composition may be an aqueous composition.

Suitable organic solvents include, but are not limited to: C1 to C4 lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglocol, polygylcerol); propylene carbonate; and mixtures thereof.

The solvent may be selected from the group consisting of water, ethanol, propanol, isopropanol, glycerol, 1,2-propylene glycol, hexylene glycol, ethoxy diglycol, and mixtures thereof.

Typically, the primer composition may comprise water as a main ingredient, particularly in a total amount ranging from at least 50%, alternatively from at least 60%, alternatively from at least 70%, by total weight of the composition. Typically, when present, the composition comprises a total amount of organic solvents ranging from about 1% to about 30%, by total weight of the composition.

Applicators

Pretreating a first portion of the hair with at least one primer composition may be carried out using an applicator such as a brush or a sponge. Alternatively, pretreating may be carried out by spraying or foaming the primer composition to the hair or by dipping the hair into the primer composition. Alternatively, pretreating may be carried out using printing technology.

Pretreatment Duration

Pretreating a first portion of the hair with at least one primer composition may comprise contacting the first portion of the hair with the primer composition. Contacting the first portion of the hair with the primer composition may comprise immersing the first portion of the hair with the primer composition for 0.5 to 60 minutes, alternatively for 1 to 45 minutes, alternatively for 2 to 30 minutes.

Other Ingredients of the Primer Composition

The primer composition according to the present invention may comprise, in addition to the ingredients indicated above, further ingredients in order to further enhance the properties of the composition, as long as these are not excluded by the claims.

Suitable further ingredients include, but are not limited to: oxidizing agents; reducing agents, alkalizing agents; oxidative dye precursors, direct dyes; chelants; radical scavengers; thickeners and/or rheology modifiers; carbonate ion sources; peroxymonocarbonate ion sources; and mixtures thereof; fragrances; enzymes; dispersing agents; peroxide stabilizing agents; antioxidants; natural ingredients (such as plant extracts); ceramides; preserving agents; opacifiers and pearling agents (such as titanium dioxide and mica); and mixtures thereof.

Particularly preferred further ingredients comprise alkalizing agents, pH modifiers and/or buffering agents, thickeners and/or rheology modifiers, and any combination thereof. Details of these components are described further below.

Polymeric Pretreatment

According to an embodiment, a first and a second primer composition may be used, wherein the first and second primer composition comprises different uncoloured polymers. For example, a first primer composition may include cationic polymers and the second primer composition comprises anionic polymers. The first and second primer compositions are subsequently applied to form an uncoulered polymeric double layer system comprising a first uncoulered cationic polymeric layer or sublayer and a second uncoloured anionic polymeric layer or sublayer. The steps can be repeated at least once to obtain two uncoulered polymeric double layers.

Any of the below described cationic and anionic polymers can be used.

Hair Colouring System

The hair colouring system used in step c) of the present invention comprises at least one cationic polymer. Specifically, the hair colouring system may comprise a first composition and a second composition. While the first composition may comprise at least one cationic polymer as described herewith, the second composition may comprise at least one anionic polymer as described herewith.

The system may further comprise a third, a fourth, a fifth, a sixth, a seventh, an eighth, a ninth and/or a tenth composition. Each of these compositions may be first or second compositions as defined herein.

For instance, the system of the present invention may comprise:
  at least a first composition comprising at least one coloured cationic polymer with a labelling degree as defined herein and/or at least one uncoloured cationic polymer as defined herein.

For instance, the system of the present invention may comprise:
  at least a first composition comprising at least one coloured cationic polymer with a labelling degree as defined herein and/or at least one uncoloured cationic polymer as defined herein, and
  at least a second composition comprising at least one coloured anionic polymer with a labelling degree as defined herein and/or at least one or uncoloured anionic polymer as defined herein.

For instance, the system of the present invention may comprise:
  a first composition comprising at least one coloured cationic polymer with a labelling degree as defined herein and/or at least one uncoloured cationic polymer as defined herein,
  a second composition comprising at least one coloured anionic polymer with a labelling degree as defined herein and/or at least one uncoloured anionic polymer as defined herein,
  a third composition comprising at least one coloured cationic polymer with a labelling degree as defined herein and/or at least one uncoloured cationic polymer as defined herein, and
  optionally a fourth composition comprising at least one coloured anionic polymer with a labelling degree as defined herein and/or at least one uncoloured anionic polymer as defined herein. As such, the coloured cationic polymers of the first and third compositions may be the same or different. Similarly, the anionic polymers of the second and fourth compositions may be the same or different. As such, the third and fourth compositions may have the same or different solvents, polymer concentrations, pH values, salt concentrations, and further ingredients as the respective first and second compositions.

Cationic Polymer

The cationic polymer which is comprised in the first composition may be selected from the group consisting of cationic coloured polymers, cationic uncoloured polymers and mixtures thereof.

Each of the cationic polymers which are comprised in each of the first compositions of step c1) and of the repeated steps c1) in step c2) may be the same or different.

In step c1) and/or in each of the repeated steps c1) of step c2), the cationic polymer may be a coloured cationic polymer.

The cationic polymer according to the present invention may comprise cationic and anionic monomeric units as long as the overall charge at full protonation is positive. As such, the following applies: $C_1 > C_2$, with $C_1$ being the total number of cationic charges and $C_2$ being the total number of anionic charges within one cationic polymer at full protonation.

The cationic polymer may comprise at least one monomer unit, i.e. one or more monomer unit(s), comprising at least one, i.e. one or more, amino functional group(s). The amino functional group(s) may be selected from the group consisting of primary, secondary, tertiary, quaternary amino functional groups and mixtures thereof. Alternatively, the amino functional group may be selected from the group consisting of primary, secondary amino functional groups and mixtures thereof. Alternatively, the amino functional group may be selected from secondary amino functional groups.

The cationic polymer may have a charge density at full protonation of at least 0.3, alternatively at least 0.6, alternatively at least 0.8, alternatively at least 1.0 positive charges per monomer unit.

The cationic polymer may have a weight average molecular weight of more than 0.5 kDa, alternatively from 0.5 to 5000 kDa, alternatively from 2 to 4000 kDa, alternatively from 5 to 3000 kDa, alternatively from 10 to 2000 kDa, alternatively from 10 to 1000 kDa, alternatively from 15 to 500 kDa, alternatively from 20 to 100 kDa, alternatively from 25 to 70 kDa.

The cationic polymer may be selected from the group consisting of linear polyethyleneimine (linear PEI), branched polyethyleneimine (branched PEI), polyallylamine hydrochloride (PAH), polydiallyldimethylammonium chloride (PDADMAC), copolymers thereof and mixtures thereof.

The first cationic polymer(s) may preferably be selected from the group consisting of polyethyleneimine, copolymers thereof and mixtures thereof.

The copolymers may be random or block copolymers.

The first cationic polymer(s) may be linear or branched.

The cationic polymer may be selected from the group consisting of:

a) Linear polyethyleneimine of the formula:

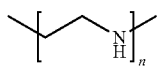

in which n is an integer representing the degree of polymerization, wherein n ranges from 50 to 20,000, alternatively from 100 to 3,500;

b) Branched polyethyleneimine consisting of primary, secondary and tertiary amine groups of the formula:

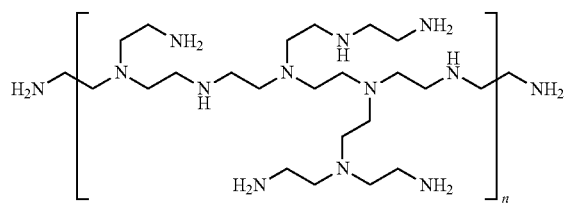

in which n is an integer representing the degree of polymerization, wherein n ranges from 5 to 4,000, alternatively from 10 to 4,000, alternatively from 50 to 1,000, alternatively from 50 to 500;

c) Polyallylamine hydrochloride (PAH) of the formula:

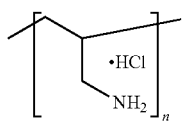

in which n is an integer representing the degree of polymerization, wherein n ranges from 50 to 20,000, alternatively from 150 to 2000, alternatively from 150 to 800;

d) Polydiallyldimethylammonium chloride (PDADMAC) of the formula:

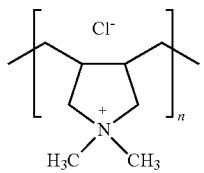

in which n is an integer representing the degree of polymerization, wherein n ranges from 50 to 20,000, alternatively from 150 to 4,000; and e) copolymers thereof and mixtures thereof.

The cationic polymer may comprise one or more compounds selected from the group consisting of cosmetically active molecules, care ingredients, optically active molecules, pharmaceutical active molecules, biomarkers and mixtures thereof.

The first cationic polymer(s) may have a weight average molecular weight of more than 0.5 kD, preferably from 0.5 kD to 5000 kD, more preferably from 2 kD to 1000 kD, even more preferably from 10 kD to 200 kD, most preferably from 25 kD to 70 kD.

Anionic Polymer

The anionic polymer which is comprised in the second composition may be selected from the group consisting of coloured anionic polymers, anionic uncoloured polymers and mixtures thereof.

The anionic polymer may be a homopolymer or a heteropolymer.

The first anionic polymer(s) may comprise one or more functional group(s) per polymer chain selected from the group consisting of phenyl group, alkyl groups comprising at least 8 carbon atoms and mixtures thereof.

The anionic polymer according to the present invention may comprise cationic and anionic monomeric units as long as the overall charge at full protonation is negative. As such, the following applies: $C_1 > C_2$, with $C_1$ being the total number of anionic charges and $C_2$ being the total number of cationic charges within one anionic polymer at full deprotonation.

The anionic polymer may have a charge density at full deprotonation of at least 0.3, alternatively at least 0.6, alternatively at least 0.8, alternatively at least 1.0 negative charges per monomer unit.

The anionic polymer may have a weight average molecular weight of at least 1 kDa, alternatively from 10 kDa to 1000 kDa, alternatively from 20 to 800 kDa, alternatively from 30 to 500 kDa, alternatively from 70 to 500 kD, alternatively from 70 to 200 kDa.

The anionic polymer may be selected from the group consisting of a biopolymers, synthetic polymers, and mixtures thereof.

Synthetic polymers may be selected from the group consisting of polystyrene sulfonate salts, polyacrylic acid, poly(methacrylic acid) salts, alginic acid salts, carboxymethylcellulose salts, PVA (Polyvinylalcohol), Polyvinylpyrrolidon-co-vinylimidazol, PSS-co-maleic acid, polystyrene sulfonate/polystyrene copolymer salts, polystyrene sulfonate/maleic acid copolymers salts, copolymers thereof, and mixtures thereof.

Biopolymers may be selected from the group consisting of polysaccharides, carrageenans, alginates and mixtures thereof.

Polysaccharides may include Dextrans, more preferably Dextran sulfate salts.

Carrageenans may be selected from the group consisting of κ-, t- und λ-Carrageens. Most preferred Carrageenans are λ-Carrageens.

The anionic polymer may comprise at least one monomer unit comprising at least one functional group selected from the group consisting of sulfate, sulfonate, carboxylate, phosphate, phosphonate groups and mixtures thereof. Alternatively, the functional group may be selected from the group consisting of sulfate, sulfonate, carboxylate groups and mixtures thereof.

The first anionic polymer(s) may be linear or branched.

The anionic polymers may be selected from the group consisting of:

a) Polystyrene sulfonate (PSS) sodium salt of the formula:

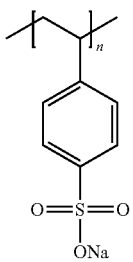

in which n is an integer representing the degree of polymerization, wherein n ranges from 50 to 20,000, alternatively from 150 to 2500, alternatively from 150 to 500;

b) Co-polymer of polystyrene sulfonate (PSS) sodium salt and poly(4-styrenesulfonic acid-co-maleic acid) of the formula:

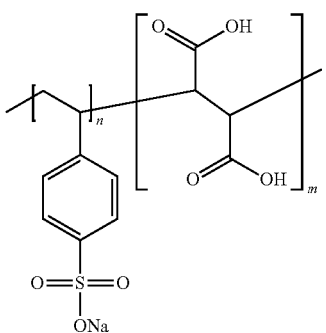

in which n and m are integers representing the degree of polymerization, wherein n+m ranges from 50 to 20,000, alternatively from 150 to 2500, alternatively from 150 to 500;

c) λ-Carrageenan;

d) Dextran sulfate sodium salt;

e) Polyacrylic acid (PAA) of the formula:

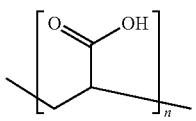

in which n is an integer representing the degree of polymerization, wherein n ranges from 50 to 20,000, alternatively from 150 to 1,000;

f) Alginic acid sodium salt;

g) Carboxymethylcellulose sodium salt of the formula:

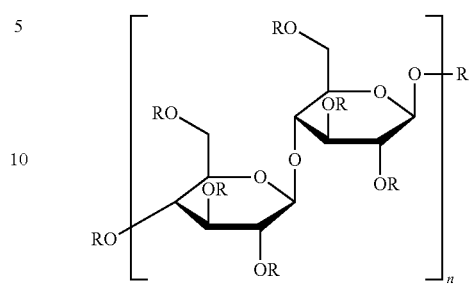

in which R is H or $(CH_2)_2COONa$ and n is an integer representing the degree of polymerization; copolymers thereof and mixtures thereof.

The copolymers may be random or block copolymers.

The anionic polymers may comprise one or more compounds selected from the group consisting of cosmetically active molecules, care ingredients, optically active molecules, pharmaceutical active molecules, biomarkers and mixtures thereof.

Coloured Cationic Polymers and Coloured Anionic Polymers

The coloured cationic polymers and the coloured anionic polymers comprise at least one chromophore and/or at least one fluorophore. Any of the hereinbefore exemplified cationic polymers or anionic polymers can comprise at least one chromophore and/or at least one fluorophore either in the skeleton or as pendent group of the polymeric backbone. For instance, the coloured cationic polymer which may be comprised in the first composition may comprise a cationic polymer, and at least one chromophore and/or at least one fluorophore. The cationic polymer is the polymeric backbone of the coloured cationic polymer and may be a cationic homopolymer or a cationic heteropolymer. The cationic polymers may be linear or branched.

The chromophores may be selected from the group consisting of radicals derived from nitrobenzene, azo, imine, hydrazine, phenothiazine, xanthene, phenanthridine, phthalocyanin and triarylmethane-based dyes, and those obtained from direct dyes containing a carbonyl group and mixtures thereof. The chromophores may be selected from the group consisting of radicals derived from acridone, benzoquinone, anthraquinone, naphthoquinone, benzanthrone, anthranthrone, pyranthrone, pyrazolanthrone, pyrimidinoanthrone, flavanthrone, indanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin dyes, and mixtures thereof.

The chromophores may be substituted with at least one amine, hydroxyl, sulfate, sulfonate, carboxylate, phosphate, phosphonate, or halide group. These chromophores may be selected from the group consisting of radicals derived from acidic nitro direct dyes, acidic azo dyes, acidic azine dyes, acidic triarylmethane dyes, acidic indoamine dyes and nonquinone acidic natural dyes, and mixtures thereof.

The chromophores may also be selected from derivatives of any of the direct dyes exemplified in the direct dyes section of this application.

The fluorophores may be selected from the group consisting of radicals derived from di-, tetra- or hexa-sulfonated triazine-stilbenes, coumarins, imidazolines, diazoles, triazoles, benzoxazolines, biphenyl-stilbenes optical brighteners, and mixtures thereof.

The coloured cationic polymer and/or the coloured anionic polymer may comprise the same type of chromophore and/or fluorophore or different types of chromophores and/or fluorophores.

The chromophores and/or fluorophores of the coloured cationic polymers and/or the coloured anionic polymers may be anionic, cationic, non-ionic, amphoteric or any combination thereof.

For instance, the coloured cationic polymers and/or the coloured anionic polymers may comprise at least one first chromophore that is anionic, cationic, non-ionic or amphoteric, and at least one second chromophore that is anionic, cationic, non-ionic or amphoteric.

Alternatively, the coloured cationic polymers and/or the coloured anionic polymers may comprise at least one first fluorophore that is anionic, cationic, non-ionic or amphoteric, and at least one second fluorophore that is anionic, cationic, non-ionic or amphoteric. Alternatively, the coloured cationic polymers and/or the coloured anionic polymers may comprise at least one chromophore that is anionic, cationic, non-ionic or amphoteric, and at least one fluorophore that is anionic, cationic, non-ionic or amphoteric.

Having a coloured cationic polymer and/or a coloured anionic polymer with different types of chromophores and/or fluorophores may help to cover a broad range of colour shades which can be obtained on hair which are coloured according to the method of the present wherein the first composition or the second composition comprises such a coloured cationic polymer or such a coloured anionic polymer. Specifically, choosing specific combinations of different chromophores and/or fluorophores enables the provision of various colours, shades and intensities of colour optimally tailored for the user.

The coloured cationic polymers may be selected from the group consisting of:
1. Coloured linear or branched polyethyleneimine (PEI) of the formula:

in which n and m are integers representing the degree of polymerization, wherein m/n ranges from 0 to 1,000 provided that n is different from 0 and/or m+n ranges from 50 to 20,000, alternatively from 100 to 3,500;
2. Coloured Polyallylamine Hydrochloride of the Formula:

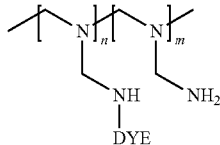

in which n and m are integers representing the degree of polymerization, wherein m/n ranges from 0 to 1,000 provided that n is different from 0 and/or m+n ranges from 50 to 20,000, alternatively from 150 to 2000, alternatively from 150 to 800;

3. Coloured polydiallyldimethylammonium chloride of the formula:

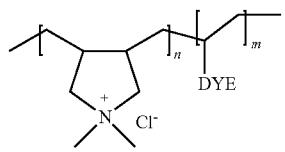

in which n and m are integers representing the degree of polymerization, wherein m/n ranges from 0 to 1,000 provided that n is different from 0 and/or m+n ranges from 10 to 20,000, alternatively 50 to 20,000, alternatively from 100 to 4000, alternatively from 100 to 3,500;
wherein DYE represents the chromophore or the fluorophore that is attached to the polymer skeleton either directly or via a saturated or unsaturated, linear or branched hydrocarbon-based chain containing from 1 to 10 carbon atoms or from 1 to 6 carbon atoms. These polymers may be block copolymers or random copolymers.

The coloured cationic polymers may be selected from linear polyethyleneimine (PEI)—Rhodamine B of the formula:

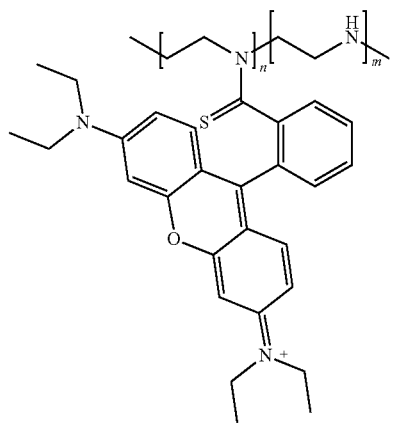

in which n and m are integers representing the degree of polymerization, wherein m/n may range from 0 to 1,000 provided that n is different from 0 and/or m+n may range from 50 to 20,000, alternatively from 100 to 3,500. These polymers may be block copolymers or random copolymers.

The coloured anionic polymers may be selected from coloured anionic polymers with the following formula:

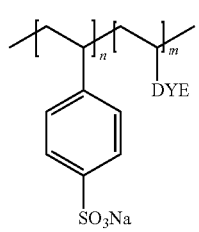

in which n and m are integers representing the degree of polymerization, wherein m/n may range from 0 to 1,000 provided that n is different from 0 and/or m+n may range from 50 to 20,000, alternatively from 150 to 500;

wherein DYE represents the chromophore or the fluorophore that is attached to the polymer skeleton either directly or via a saturated or unsaturated, linear or branched hydrocarbon-based chain containing from 1 to 10 carbon atoms or from 1 to 6 carbon atoms. These polymers may be block copolymers or random copolymers.

Labelling Degree

The labelling degree k is a measure for the loading of a polymer with a dye. The labelling degree k is defined as n:m, with n being the number of chromophores and/or fluorophores per polymer and m being the monomeric units per polymer. As such, the higher the labelling, the higher the labelling degree, i.e. the more chromophores and/or fluorophores are present in one coloured cationic polymer. The labelling degree k may be between 1:2 to 1:100, alternatively between 1:5 to 1:90. alternatively between 1:10 to 1:80, alternatively between 1:12 to 1:70, alternatively between 1:15 to 1:70, alternatively between 1:20 to 1:60, alternatively between 1:30 to 1:50, alternatively between 1:35 to 1:45, alternatively between 1:12 to 1:30, alternatively between 1:12 to 1:20. Alternatively, the labelling degree k may be between 1:1100 to 1:1:1000,000, alternatively between 1:2000 to 1:900,000, alternatively between 1:5000 to 1:800,000, alternatively between 1:10,000 to 1:700,000, alternatively between 1:50,000 to 1:600,000, alternatively between 1:100,000 to 1:500,000, alternatively between 1:150,000 to 1:400,000, alternatively between 1:200,000 to 1:300,000.

The choice of the appropriate labelling degree primarily depends on the types of chromophores and/or fluorophores used for labelling the cationic and/or anionic polymer. For instance, when using chromophores and/or fluorophores providing per se a stronger colour intensity to hair, the labelling degree can be lower, e.g., between 1:100,000 to 1:1,000,000. On the other hand, when using chromophores and/or fluorophores providing per se a weaker colour intensity to hair, the labelling degree should be higher, e.g., between 1:2 to 1:1000.

The labelling degree may also depend on the type of polymer backbone, and more particularly on the number of possible binding positions on the polymer backbone onto which the dye can be covalently bonded. Notably, these binding positions can be activated or deactivated. For instance, deactivation can be carried out by e.g., chemically bonding specific protection groups to at least some of the binding positions. Accordingly, activation can be carried out e.g., by splitting such protection groups from the respective binding position. As such, the polymer backbone can be tailored to have the desired number of binding positions for the dye. Various other parameters help adjusting the appropriate labelling degree.

First and Second Compositions

Solvents

The first and/or the second compositions which are used in step c) to carry out the method according the present invention may further comprise a solvent. The solvent may be selected from water, or a mixture of water and at least one organic solvent to dissolve the compounds that would not typically be sufficiently soluble in water. The first and/or the second compositions may be aqueous compositions.

Suitable organic solvents include, but are not limited to: C1 to C4 lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglocol, polygylcerol); propylene carbonate; and mixtures thereof.

The solvent may be selected from the group consisting of water, ethanol, propanol, isopropanol, glycerol, 1,2-propylene glycol, hexylene glycol, ethoxy diglycol, and mixtures thereof.

Typically, the first and/or the second compositions may comprise water as a main ingredient, particularly in a total amount ranging from at least 50%, alternatively from at least 60%, alternatively from at least 70%, by total weight of the composition. Typically, when present, the first and/or the second compositions comprises a total amount of organic solvents ranging from about 1% to about 30% by total weight of the composition.

Polymer Concentrations

The first composition may comprise a total concentration of cationic polymers which is ranging from 0.1 g/L to 100 g/L, alternatively from 0.5 g/L to 100 g/L, alternatively from 2 g/L to 50 g/L, alternatively from 5 g/L to 10 g/L.

The second composition may comprise a total concentration of anionic polymers which is ranging from 0.1 g/L to 100 g/L, alternatively from 0.5 g/L to 100 g/L, alternatively from 2 g/L to 50 g/L, alternatively from 5 g/L to 10 g/L.

In preferred embodiments, the first composition may comprise a total concentration of cationic polymers which is lower than the total concentration of anionic polymers in the second composition. Alternatively, the first composition may comprise a total concentration of cationic polymers which is higher than the total concentration of anionic polymers in the second composition. Alternatively, the first composition may comprise a total concentration of cationic polymers which is equal to the total concentration of anionic polymers in the second composition.

By using different polymer concentrations in the first and second compositions, different effects can be achieved. For instance, using higher polymer concentrations in the first composition than in the second composition can result in portions of hair with bilayer structure (i.e. a structure where a coloured cationic polymer layer attached to the hair surface is covered by an anionic polymer layer) and portions of hair where no such bilayer structure is formed. By repeating applying the first composition followed by the second composition (i.e. carrying out a second treatment), only in those portions where a bilayer has formed, a second coloured cationic polymer layer can be attached to the anionic polymer layer of the bilayer structure resulting in an increase of colour intensity. On the other hand, in those portions where no bilayer has formed (i.e., where only a cationic polymer layer has been attached to the hair surface without an anionic protective layer), no second coloured cationic polymer layer can be attached, and as such, no change in colour intensity occurs. This leads to different colour intensities on different hair portions of the user which may be intentional in order to spotlight certain portions of hair. Notably, those portions of hair where no such additional second coloured cationic polymer layer could be attached due to a lack of bilayer structure will now be covered by an anionic polymer layer from the second treatment, thus forming a "delayed" bilayer structure. On this "delayed" bilayer structure, a second coloured cationic polymer layer can now be attached by repeating applying the first composition followed by the second composition once again (i.e. carrying out a third treatment). On the other hand, those portions where an additional second coloured cationic polymer layer has already been attached by the second treatment, the third treatment enables the attachment of a third coloured cationic polymer layer depending on whether or not a second anionic polymer layer covers said second coloured cationic polymer layer. To ensure the attachment of a second anionic polymer layer to the second coloured cationic polymer layer in the second treatment, the total concentration of anionic polymers in the second composition now should be higher than the total concentration of coloured cationic polymers in order to compensate the lack of anionic polymers on those portions of hair where no such bilayer structure has formed. Thus, after the third treatment, there may be portions of hair having two full bilayer structures while there may also be portions of hair having three full bilayer structures, thereby providing different colour intensities in different hair portions. After having adjusted the desired colour intensity interval between at least two portions of hair, a fourth treatment can be carried out by repeating the step of applying the first composition followed by the second composition wherein the polymer concentrations in the first and second compositions are substantially the same.

Therefore, through variation of the total polymer concentrations in the first and second compositions, different colour intensities on different hair portions can be tailored which may be desired in various cases, e.g., where hair greying takes place only in certain areas of hair such as temples etc.

pH Value

The first and/or second composition may have a pH ranging from 2 to 14, alternatively from 3 to 11, alternatively from 5 to 10, alternatively from 7 to 9.

In preferred embodiments, the first composition may have a pH that is lower than the pH of the second composition. Alternatively, the first composition may have a pH that is higher than the pH of the second composition. Alternatively, the first composition may have a pH that is equal to the pH of the second composition. In further embodiments, the first composition may have a pH different to the pH of the third composition, wherein the pH of the first composition can be higher or lower than the pH of the third composition.

Adjusting the pH values in the first and second compositions is desirable for various reasons. For instance, too extreme pH values, e.g., pH>12 or pH<3 may cause damage to the structure of the hair and may be irritating for the scalp of the user, especially when such a process is repeated more than once. On the other hand, the lower the pH of the first composition, the better the protonation of the coloured cationic polymer. This leads to a higher cationic charge which is desirable for a better attachment to the anionic hair surface. Similarly, the higher the pH of the second composition, the better the deprotonation of the anionic polymer. This leads to a higher anionic charge which is desirable for a better attachment to the coloured cationic polymer. Therefore, in principle, the first composition may have a pH that is lower than the pH of the second composition.

However, the present inventors unexpectedly found out that the colour intensity increases proportionally to the pH of the first composition. Thus, in most preferred embodiments, the first composition may have a pH that is higher than the pH of the second composition. In certain instances, while it is preferred to use a weak acidic pH in the second composition, such as a pH between 5 and 6, the pH in the first composition may be between 6 to 10, more preferably between 7 to 9.

Nevertheless, one of the advantages of the system according to the present invention is that the hair may be coloured with a good colour intensity even if both compositions which are used have a lower pH. Taking further into account the skin's natural pH levels being in the weakly acid, depending e.g. on the gender and age of the user, the pH levels of the first and second compositions can particularly be tailored for the user's need.

Salt

The first and/or the second composition may comprise a cosmetically acceptable salt at a concentration ranging from 0 to 1.5 mol/L, alternatively from 0.05 to 1 mol/L, alternatively from 0.2 to 0.5 mol/L. The first and/or the second composition may comprise the same cosmetically acceptable salt(s) or different cosmetically acceptable salt(s).

In preferred embodiments, the first composition may comprise a cosmetically acceptable salt at a concentration that is higher than the concentration of the cosmetically acceptable salt in the second composition. Alternatively, the first composition may comprise a cosmetically acceptable salt at a concentration that is lower than the concentration of the cosmetically acceptable salt in the second composition. Alternatively, the first composition may comprise a cosmetically acceptable salt at a concentration that is equal to the concentration of the cosmetically acceptable salt in the second composition.

The cosmetically acceptable salt may be selected from the group consisting of an organic salt, a mineral salt and mixture thereof. The organic salt may be sodium citrate. The mineral salt may be selected from the group consisting of sodium chloride, ammonium sulfate, magnesium chloride, calcium chloride and mixtures thereof. The cosmetically acceptable salt may be sodium chloride.

Adjusting the concentration of the cosmetically acceptable salt in the first composition is another important parameter. For instance, using higher concentrations of cosmetically acceptable salts in the first composition comprising the coloured cationic polymer (e.g. up to 1 mol/L) has the effect that a greater number of negatively charged ions can gather around each cationic polymer chain. This leads to the formation of a strong electrostatic shield around each polymer chain. The resulting decrease of positive charge in the immediate surroundings of each polymer chain has the effect that only those parts of the polymer chain which have still enough positive charge will ionically bind to the negatively charged hair surface. The number decrease of anchoring sites of each polymer chain results in an undulated orientation of each coloured cationic polymer, e.g., on the hair surface, thereby enabling the binding of a greater number of coloured cationic polymers. The greater the number of bound coloured cationic polymers on a defined hair surface portion, the more intensive the colour of this portion. Thus, adjusting the salt concentration, particularly in the first composition, may be particularly useful to modify the colour intensity.

Applicators

The first and/or the second compositions may be applied to the hair using an applicator such as a brush or a sponge. Alternatively, the first and/or the second compositions may be applied to the hair by spraying or foaming the first and/or the second compositions to the hair or by dipping the hair into the first and/or the second composition. Alternatively, the first and/or the second compositions may be applied to the hair using printing technology.

Treatment Duration

Treating a second portion of the hair with a hair colouring system may comprise applying a first composition comprising the cationic polymer to a third portion of the hair; and applying a second composition comprising at least one anionic polymer to a fourth portion of the hair; the third and fourth portions of the hair having the second portion of the hair as common area. Applying the first composition to the hair may comprise contacting the third portion of the hair with the first composition. Contacting may comprise immersing the third portion of the hair with the first composition for 0.5 to 60 minutes, alternatively for 1 to 45 minutes, alternatively for 2 to 30 minutes. Applying the second composition to the hair may comprise contacting the fourth portion of the hair with the second composition. Contacting may comprise immersing the fourth portion of the hair with the second composition for 0.5 to 60 minutes, alternatively for 1 to 45 minutes, alternatively for 2 to 30 minutes.

Hair Colouration

The present invention also relates to a hair colouration which is obtainable by the method according to the present invention. As already explained hereinbefore, the structure of the hair colouration is unique in that it is made of alternating polymeric layers which are formed by the alternate deposition of cationic polymers and anionic polymers on a pretreated hair surface.

Hair Colouring Kit

The present invention also relates to a hair colouring kit comprising a first compartment comprising the primer composition as defined hereinbefore and a second compartment comprising the hair colouring system as defined hereinbefore. Moreover, the present invention further relates to a hair colouring kit comprising a first compartment comprising the primer composition as defined hereinbefore, a second compartment comprising the first composition as defined hereinbefore, and a third compartment comprising the second composition as defined hereinbefore.

Other Ingredients

The first and/or the second compositions used in step c) according to the present invention may comprise, in addition to the ingredients indicated above, further ingredients in order to further enhance the properties of the composition, as long as these are not excluded by the claims.

Suitable further ingredients include, but are not limited to: oxidizing agents; alkalizing agents; oxidative dye precursors, direct dyes; chelants; radical scavengers; pH modifiers and buffering agents; thickeners and/or rheology modifiers; carbonate ion sources; peroxymonocarbonate ion sources; anionic, cationic, nonionic, amphoteric or zwitterionic surfactants, and mixtures thereof; anionic, cationic, nonionic, amphoteric or zwitterionic polymers, and mixtures thereof; fragrances; enzymes; dispersing agents; peroxide stabilizing agents; antioxidants; natural ingredients (such as proteins, protein compounds, and plant extracts); conditioning agents (such as silicones and cationic polymers); ceramides; preserving agents; opacifiers and pearling agents (such as titanium dioxide and mica); and mixtures thereof.

Particularly preferred further ingredients comprise alkalizing agents, pH modifiers and/or buffering agents, thickeners and/or rheology modifiers, (anionic, cationic, nonionic, amphoteric or zwitterionic) surfactants, and any combination thereof.

Suitable further ingredients referred to above, but not specifically described below, are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed hereinbelow, whose disclosure is of course non-exhaustive.

Oxidizing Agents

The first and/or the second compositions used in step c) according to the present invention may further comprise at least one source of an oxidizing agent. Any oxidizing agent known in the art may be used. Preferred oxidizing agents are water-soluble peroxygen oxidizing agents. As used herein, "water-soluble" means that in standard conditions at least 0.1 g, preferably about 1 g, more preferably 10 g of the oxidizing agent can be dissolved in 1 liter of deionized water at 25° C. The oxidizing agents are valuable for the initial solubilisation and decolourisation of the melanin (bleaching) and accelerate the oxidation of the oxidative dye precursors (oxidative dyeing) in the hair shaft.

The first and/or the second compositions may comprise a total amount of oxidizing agents ranging from 0.1% to 10%, alternatively from 1% to 7%, alternatively from 2% to 5%, by total weight of the composition.

The first and/or the second compositions may comprise a total amount of oxidizing agents ranging from 0.1% to 3%, alternatively from 0.2% to 2%, alternatively from 0.3% to 2%, by total weight of the composition.

Suitable water-soluble oxidizing agents include, but are not limited to: inorganic peroxygen materials capable of yielding hydrogen peroxide in an aqueous solution.

Alternatively, the first and/or the second compositions may comprise a total amount of oxidizing agents of less than 1%, alternatively less than 0.5%, alternatively less than 0.3%, alternatively less than 0.1% by total weight of the composition. Alternatively, the first and/or the second compositions may be free of oxidizing agents. By having the first and/or the second compositions which comprise a low amount of oxidizing agents or even no oxidizing agents, these compositions are usually less damaging the hair than standard hair colouring composition which usually comprise a high concentration of oxidizing agent.

Suitable water-soluble peroxygen oxidizing agents include, but are not limited to: hydrogen peroxide; inorganic alkali metal peroxides (such as sodium periodate and sodium peroxide); organic peroxides (such as urea peroxide and melamine peroxide); inorganic perhydrate salt bleaching compounds (such as the alkali metal salts of perborates, percarbonates, perphosphates, persilicates, persulphates and the like); and mixtures thereof. Inorganic perhydrate salts may be incorporated for example as monohydrates, tetrahydrates. Alkyl/aryl peroxides and/or peroxidases may also be used. Mixtures of two or more such oxidizing agents can be used if desired.

The oxidizing agents may be provided in aqueous solution or as a powder which is dissolved prior to use.

The first and/or the second compositions may comprise a water-soluble oxidizing agent selected from the group consisting of hydrogen peroxide, percarbonates (which may be used to provide a source of both oxidizing agent and carbonate ions and or ammonium ions), persulphates, and mixtures thereof.

When the first and/or the second compositions of the present invention are obtained by mixing a developer composition and a tint composition prior to use, the oxidizing agent may be present in the developer composition. The developer composition may be based on any desired formulation chassis, including any commercial product, for example an oil-in-water emulsion. Typical developer compositions comprise about 6% or about 9% of the $H_2O_2$ relative to the total weight of the developer composition. A commercial example is the Welloxon® Emulsion with respectively about 6% and about 9% $H_2O_2$, marketed by Wella and comprising as INCI ingredients: Water, $H_2O_2$, Cetearyl Alcohol, Ceteareth-25, Salicylic Acid, Phosphoric Acid, Disodium Phosphate, Etidronic Acid.

Alkalizing Agents

Alkalizing agents are particularly useful to adjust the pH value in the first and second compositions which—as described in detail uner the headline "pH Value"—is inter alia an important parameter for controlling the colour intensity of hair.

The first and/or the second compositions according to the present invention may further comprise at least one alkalizing agent. Any alkalizing agent known in the art may be used.

Typically, the first and/or the second compositions may comprise a total amount of alkalizing agents ranging from 0.1% to 10%, alternatively from 0.5% to 6%, alternatively from 1% to 4%, by total weight of the composition.

Alternatively, the first and/or the second compositions may comprise a total amount of alkalizing agents of less than 1%, alternatively less than 0.5%, alternatively less than 0.3%, alternatively less than 0.1% by total weight of the composition. Alternatively, the first and/or the second compositions may be free of alkalizing agents. Suitable alkalizing agents include, but are not limited to: ammonia; alkanolamines (such as monoethanolamine, diethanolamine, triethanolamine, monopropanolamine, dipropanolamine, tripropanolamine 2-amino-2-methyl-1,3-propanediol, 2-amino-2-methyl-1-propanol, and 2-amino-2-hydroxymethyl-1,3-propanediol); guanidium salts; alkali metal and ammonium hydroxides (such as sodium hydroxide); alkali metal and ammonium carbonates; and mixtures thereof. Typical alkalizing agents are ammonia and/or monoethanolamine.

The first and/or the second compositions may comprise a total amount of ammonia of less than 1%, alternatively less than 0.5%, alternatively less than 0.3%, alternatively less than 0.1% by total weight of the composition. Alternatively, the first and/or the second compositions may be free of ammonia. These embodiments are particularly interesting in that such compositions are odourless.

Preferably, if present, the ammonium ions and carbonate ions are present in the composition at a weight ratio of from 3:1 to 1:10, alternatively from 2:1 to 1:5.

When the compositions of the present invention is obtained by mixing a developer and a tint composition prior to use, the alkalizing agent is generally present in the tint composition.

Oxidative Dye Precursors

The first and/or the second compositions used in step c) according to the present invention may further comprise oxidative dye precursors, which are usually classified either as primary intermediates (also known as developers) or couplers (also known as secondary intermediates). Various couplers may be used with primary intermediates in order to obtain different shades. Oxidative dye precursors may be free bases or the cosmetically acceptable salts thereof.

Typically, the first and/or the second compositions may comprise a total amount of oxidative dye precursors ranging up to 12%, alternatively from 0.1% to 10%, alternatively from 0.3% to 8%, alternatively from 0.5% to 6%, by total weight of the composition.

Suitable primary intermediates include, but are not limited to: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino) ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, 2-[(3-aminopyrazolo[1,5-a]pyridin-2-yl)oxy] ethanol hydrochloride, salts thereof and mixtures thereof.

Suitable couplers include, but are not limited to: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis (azanediyl)diethanol, benzene-1,3-diamine, 2,2'-(4,6-diamino-1,3-phenylene)bis(oxy)diethanol, 3-(pyrrolidin-1-yl) aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methyl amino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

When the compositions are obtained by mixing a tint composition and a developer composition, the primary intermediates and couplers are usually incorporated into the tint composition.

Direct Dyes

The first and/or the second compositions according to the present invention may further comprise compatible direct dyes, in an amount sufficient to provide additional colouring, particularly with regard to intensity. Typically, the first and/or the second compositions may comprise a total amount of direct dyes ranging from about 0.05% to about 4%, by total weight of the composition.

Suitable direct dyes include but are not limited to: Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, Basic Blue 124, 4-(3-(4-amino-9,10-dioxo-9,10-di hydroanthracen-1-yl amino)propyl)-4-methylmorpholin-4-ium-methylsulfate, (E)-1-(2-(4-(4,5-dimethylthiazol-2-yl)diazenyl)phenyl)

(ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14; Natural dyes such as Annato, Anthocyanin, Beetroot, Carotene, Capsanthin, Lycopene, Chlorophyll, Henna, Indigo, Cochineal; and mixtures thereof.

When the compositions are obtained by mixing a tint composition and a developer composition, the direct dyes are usually incorporated into the tint composition.

Chelants

The first and/or the second compositions used in step c) according to the present invention may further comprise chelants (also known as "chelating agent", "sequestering agent", or "sequestrant") in an amount sufficient to reduce the amount of metals available to interact with formulation components, particularly oxidizing agents, more particularly peroxides. Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996), both incorporated herein by reference.

Typically, the first and/or the second compositions may comprise a total amount of chelants ranging from at least 0.01%, alternatively from 0.01% to 5%, alternatively from 0.25% to 3%, alternatively from 0.5% to 1%, by total weight of the composition.

Suitable chelants include, but are not limited to: carboxylic acids (such as aminocarboxylic acids), phosphonic acids (such as aminophosphonic acids), polyphosphoric acids (such as linear polyphosphoric acids), their salts thereof, and mixtures thereof. By "salts thereof", it is meant—in the context of chelants—all salts comprising the same functional structure as the chelant they are referring to and including alkali metal salts, alkaline earth salts, ammonium salts, substituted ammonium salts, and mixtures thereof: alternatively sodium salts, potassium salts, ammonium salts, and mixtures thereof; alternatively monoethanolammonium salts, diethanolammonium salts, triethanolammonium salts, and mixtures thereof.

Suitable aminocarboxylic acid chelants comprise at least one carboxylic acid moiety (—COOH) and at least one nitrogen atom. Suitable aminocarboxylic acid chelants include, but are not limited to: diethylenetriamine pentaacetic acid (DTPA), ethylenediamine disuccinic acid (EDDS), ethylenediamine diglutaric acid (EDGA), 2-hydroxypropylenediamine disuccinic acid (HPDS), glycinamide-N,N'-disuccinic acid (GADS), ethylenediamine-N—N'-diglutaric acid (EDDG), 2-hydroxypropylenediamine-N—N'-disuccinic acid (HPDDS), ethylenediaminetetraacetic acid (EDTA), ethylenedicysteic acid (EDC), ethylenediamine-N—N'-bis(ortho-hydroxyphenyl acetic acid) (EDDHA), diaminoalkyldi(sulfosuccinic acids) (DDS), N,N'-bis(2-hydroxybenzyl)ethylenediamine-N, N'-diacetic acid (HBED), their salts thereof, and mixtures thereof. Other suitable aminocarboxylic type chelants include, but are not limited to: iminodiacetic acid derivatives such as N-2-hydroxyethyl N,N diacetic acid or glyceryl imino diacetic acid, iminodiacetic acid-N-2-hydroxypropyl sulfonic acid and aspartic acid N-carboxymethyl N-2-hydroxypropyl-3-sulfonic acid, β-alanine-N,N'-diacetic acid, aspartic acid-N,N'-diacetic acid, aspartic acid-N-monoacetic acid and iminodisuccinic acid chelants, ethanoldiglycine acid, their salts thereof, their derivatives thereof, and mixtures thereof. Further suitable aminocarboxylic type chelants include, but are not limited to: dipicolinic acid, 2-phosphonobutane-1,2,4-tricarboxylic acid, their salts thereof, their derivatives thereof, and mixtures thereof.

Suitable aminophosphonic acid chelants comprise an aminophosphonic acid moiety (—PO$_3$H$_2$) or its derivative —PO$_3$R$_2$, wherein R$_2$ is a C$_1$ to C$_6$ alkyl or aryl radical and salts thereof. Suitable aminophosphonic acid chelants include, but are not limited to: aminotri-(1-ethylphosphonic acid), ethylene-diaminetetra-(1-ethylphosphonic acid), aminotri-(1-propylphosphonic acid), aminotri-(isopropylphosphonic acid), their salts thereof, and mixtures thereof; alternatively aminotri-(methylenephosphonic acid), ethylenediamine-tetra-(methylenephosphonic acid) (EDTMP) and diethylene-triamine-penta-(methylenephosphonic acid) (DTPMP), their salts thereof, their derivatives thereof, and mixtures thereof.

Suitable alternative chelants include, but are not limited to: polyethyleneimines, polyphosphoric acid chelants, etidronic acid, methylglycine diacetic acid, N-(2-hydroxyethyl)iminodiacetic acid, minodisuccinnic acid, N,N-Dicarboxymethyl-L-glutamic acid, N-lauroyl-N,N',N''-ethylenediamine diacetic acid, their salts thereof, their derivatives thereof, and mixtures thereof.

In a specific embodiment, the composition comprises a chelant selected from the group consisting of diethylenetriamine-N,N',N''-polyacids, diethylenetriaminepentaacetic acid (DTPA), diethylenetriaminepenta(methylene phosphonic acid) (DTPMP), diamine-N,N'-dipolyacid, monoamine monoamide-N,N'-dipolyacid, ethylenediaminedisuccinic acid (EDDS), their salts thereof, their derivatives thereof, and mixtures thereof; alternatively ethylenediaminedisuccinic acid (EDDS).

When the compositions of the invention are obtained by mixing a tint composition and a developer composition, the chelants may be incorporated in the tint composition and/or in the developer composition. A chelant is usually present in the developer composition for stability reason.

Radical Scavengers

The first and/or the second compositions used in step c) according to the present invention may further comprise a radical scavenger. As used herein the term "radical scavenger" refers to a species that can react with a radical, preferably a carbonate radical to convert the radical species by a series of fast reactions to a less reactive species. In one embodiment, the radical scavenger is different from the alkalising agent and/or is present in an amount sufficient to reduce the damage to the hair during the colouring/bleaching process.

Typically, the first and/or the second compositions may comprise a total amount of radical scavengers ranging from 0.1% to 10%, alternatively from 1% by weight to 7%, by total weight of the composition.

Suitable radical scavengers include, but are not limited to: alkanolamines, amino sugars, amino acids, esters of amino acids, and mixtures thereof; alternatively 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, their salts thereof, and mixtures thereof; alternatively glycine, sarcosine, lysine, serine, 2 methoxyethylamine, glucosamine, glutamic acid, morpholine, piperdine, ethylamine, 3 amino-1-propanol, and mixtures thereof. As used herein, the term "salts thereof"—in the context of radical scavengers—means particularly potassium salts, sodium salts, ammonium salts, and mixtures thereof, pH Modifiers and buffering agents Similar to alkalizing agents, pH modifiers and buffering agents are particularly useful to adjust the pH value in the first and second compositions which—as described in detail uner the headline "pH Value"—is inter alia an important parameter for controlling the colour intensity of hair.

The first and/or the second compositions according to the present invention may further comprise, in addition to the alkalizing agent discussed above, a pH modifier and/or buffering agent.

Suitable pH modifiers and/or buffering agents include, but are not limited to: ammonia; alkanolamides (such as monoethanolamine, diethanolamine, triethanolamine, monopropanolamine, dipropanolamine, tripropanolamine, tripropanolamine, 2-amino-2-methyl-1-propanol, 2-amino-2-hydroxymethyl-1,3,-propandiol); guanidium salts; alkali metal and ammonium hydroxides and carbonates; and mixtures thereof.

Further pH modifiers and/or buffering agents include, but are not limited to: sodium hydroxide; ammonium carbonate; acidulents (such as inorganic and inorganic acids including for example phosphoric acid, acetic acid, ascorbic acid, citric acid or tartaric acid, hydrochloric acid); and mixtures thereof. Thickeners and/or rheology modifiers The first and/or the second compositions used in step c) according to the invention may further comprise a thickener in an amount sufficient to provide the compositions with a viscosity so that it can be readily applied to the hair without unduly dripping off the hair and causing mess.

Typically, the first and/or the second compositions may comprise a total amount of thickeners ranging from at least 0.1%, alternatively at least 0.5%, alternatively at least 1%, by total weight of the composition.

Suitable thickeners include, but are not limited to: associative polymers, polysaccharides such as hydroxyethylcellulose, non-associative polycarboxylic polymers, and mixtures thereof.

Thickeners and/or rheology modifiers in the first and second compositions may have a beneficial impact on the final colour intensity of hair. In principle, the more viscous the composition is, the better is the adherence of the respective polymers to the target surface (e.g., hair surface or polymer chain), For instance, the more viscous the first composition is, the better is the adherence of the coloured cationic polymer on hair. This results in a better interaction between hair and polymer, thereby assisting in achieving a more intensive colour. However, it is not desirable to use an excessive amount of thickeners in the first and/or second compositions since this would hamper the natural diffusion of the respective polymers, thereby limiting the contact times with the target surface. Therefore, a well-balanced concentration of thickeners helps to better control the colour intensity of hair.

Carbonate Ion Sources

The first and/or the second compositions used in step c) according to the present invention may further comprise a source of carbonate ions, carbamate ions, hydrogen carbonate ions, and mixtures thereof in a sufficient amount to reduce damage to the hair during the colouring process.

Typically, the first and/or the second compositions may comprise a total amount of a carbonate ion source ranging from 0.1% to 15%, alternatively from 0.1% to 10%, alternatively from 1% to 7%, by total weight of the composition.

Suitable carbonate ion sources include, but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof; alternatively sodium hydrogen carbonate, potassium hydrogen carbonate, and mixtures thereof, alternatively ammonium carbonate, ammonium hydrogen carbonate, and mixtures thereof.

Conditioning Agents

The first and/or the second compositions used in step c) according to the present invention may further comprise a conditioning agent, and/or be used in combination with a composition comprising a conditioning agent.

Typically, the first and/or the second compositions may comprise a total amount of conditioning agents ranging from 0.05% to 20%0, alternatively from 0.1% to 15%, alternatively from 0.2% to 10%, alternatively from 0.2% to 2%, alternatively from 0.5% to 2%, by total weight of the composition. The conditioning agent may be included in a separate pre- and/or post-treatment composition.

Suitable conditioning agents include, but are not limited to: silicones, aminosilicones, fatty alcohols, polymeric resins, polyol carboxylic acid esters, cationic polymers, cationic surfactants, insoluble oils and oil derived materials and mixtures thereof. Additional conditioning agents include mineral oils and other oils such as glycerine and sorbitol.

Surfactants

Surfactants help solubilizing the polymers in the solvent. This is particularly important when using polymers (e.g., coloured cationic polymers) having a high weight average molecular weight, e.g. up to 5000 kDa otherwise undesired precipitation might occur.

The first and/or the second compositions according to the present invention may further comprise a surfactant. Suitable surfactants generally have a lipophilic chain length of from about 8 to about 30 carbon atoms and can be selected from anionic surfactants, nonionic surfactants, amphoteric surfactants, cationic surfactants, and mixtures thereof. Depending on their ionic (or non-ionic) character, surfactants can help adjusting the ionic strength of the first and/or second compositions which may affect the resultant viscosity and root adhesion properties of the respective composition.

Typically, the first and/or the second compositions may comprise a total amount of surfactants ranging from 1% to 60%, alternatively from 2% to 30%, alternatively from 8% to 25%0, alternatively from 10/to 20%, by total weight of the composition.

The first and/or the second compositions may comprise a mixture of an anionic surfactant and an amphoteric surfactant with one or more nonionic surfactants. Alternatively, the first and/or the second compositions may comprise a mixture of a cationic surfactant and an amphoteric surfactant with one or more nonionic surfactants.

The first and/or the second compositions may comprise a total amount of anionic surfactants ranging from 0.1% to 20%, alternatively from 0.1% to 15%, alternatively from 5% to 15%, by total weight of the compositions; and a total amount of amphoteric and/or nonionic components, which may range independently from each other from 0.1% to 15%, alternatively from 0.5% to 10%, alternatively from 1% to 8%, by total weight of the compositions.

Ionic Strength

The first and/or the second compositions used in step c) of the present invention may further have an ionic strength as defined herein of less than about 1.35 mole/kg, alternatively from about 0.10 to about 0.75 mole/kg, alternatively from about 0.20 to about 0.60 mole/kg. Whilst not being bound by theory, it is believed that the ionic strength value may also affect the resultant viscosity and root adhesion properties of the composition. The ionic strength can be affected by salt resources such as the dyes, sodium sulphate, ammonium carbonate anti-oxidants and chelants such as EDDS, as well as surfactants. The dye tends to have the greatest effect on the ionic strength and thus the amounts added in order to provide any particular shade need to be considered in terms of ionic strength as well as dye outcome in order to prevent viscosity and root adhesion problems.

The ionic strength of the compositions is a function of the concentration of all ions present in that solution and is determined according to the formula:

$$I = \frac{1}{2}\sum_{i=1}^{n} m_i z_i^2$$

where $m_i$=molality of ion i (M=mol·/Kg $H_2O$), $z_i$=charge number of that ion, and the sum is taken over all ions in the solution. For example, for a 1:1 electrolyte such as sodium chloride, the ionic strength is equal to the concentration, but for $MgSO_4$ the ionic strength is four times higher. Generally multivalent ions contribute strongly to the ionic strength.

For example the ionic strength of a mixed 0.050 M $Na_2SO_4$ and 0.020 M NaCl solution is: I=½((2×(+1)²×0.050)+(+1)²×0.020+(−2)²×0.050+(−1)²×0.020)=0.17 M.

Foam

The first and/or second compositions used in step c) of the invention may be provided in the form of foam which is applied to the hair. Foam formation is typically achieved by the use of a foaming agent incorporated within the composition in combination with a manually operated foaming device. Such manually operated foaming devices are known in the art and include aerosols devices, squeeze foamers and pump foamers.

Suitable foaming agents includes surfactants such as anionic, nonionic and amphoteric surfactants, nonionic surfactants being preferred; polysaccharides; polyvinyl pyrrolidone and copolymers thereof; acrylic polymers such as Acrylates copolymer (Aculyn 33) and Acrylates/Steareth-20 methacrylates (Aculyn 22); C12-C24 fatty acids such as stearates and mixtures thereof.

EXAMPLES

The following are non-limiting examples of compositions of the present invention. The examples are given solely for the purpose of illustration and are not to be construed as limitations of the present invention, as many variations thereof are possible without departing from the spirit and scope of the invention, which would be recognized by one of ordinary skill in the art.

In the following section the solvent used to prepare the different compositions is water, unless otherwise specified.

1. Synthesis Methods for Obtaining the Cationic Coloured Polymers Used in the Examples:

Cationic Coloured Polymers

Branched polvethyleneimine labeled with Red 4B:
  Starting materials:
    Branched polyethyleneimine (PEI), LUPASOL WF, Mw=25.000 Da available from BASF (CAS: 9002-98-6)
    EverPlus Red 4B Powder available from Everlight Chemicals
  Synthesis method:
  The following method has been used for labeling Branched polyethyleneimine (PEI) with EverPlus Red 4B:
    1) Dissolving 10 g branched polyethyleneimine (PEI) in a 400 ml aqueous solution containing 13.95 EverPlus Red 4B;
    2) Stirring the suspension at 60° C. for 1 hour;
    3) Further stirring the resultant mixture at room temperature for 12 h;
    4) Centrifuging the resultant mixture and collecting the supernatant;
    5) Evaporate the collected supernatant to dryness;
    6) Adding 200 mL methanol to re-dissolve the solid completely;
    7) Adding 25.43 ml of a 32 wt % hydrochloric acid solution to the resulting mixture from step 6);
    8) Centrifuging the resulting suspension and collecting the precipitate;
    9) Washing the precipitate with acetone until the supernatant is colorless;
    10) Drying the precipitate and dissolving it in water;
    11) Dialyzing the resulting solution against a solution of 0.15 M NaCl and 10' to $10^{-5}$ M HCl;
    12) Freeze-drying the product.

Branched polvethyleneimine labeled with Red 180:
  Starting materials:
    Branched polyethyleneimine (PEI) (LUPASOL G 500), Mw=25,000 Da, available from BASF (CAS: 9002-98-6)
    Reactive Red 180 available from S3 Chemicals (CAS: 72828-03-6).

Synthesis method:

The following method has been used for labeling branched polyethyleneimine (PEI) with Reactive Red 180 (Red):

1) Dissolving 12.5 g of a 40 wt % solution of Branched polyethyleneimine (PEI) in a 200 ml methanol solution containing 14.05 g of Reactive Red 180;
2) Stirring the suspension at 60° C. for 1 hour;
3) Further stirring the resultant mixture at room temperature for 12 h;
4) Centrifuging the resultant mixture and collecting the supernatant;
5) Adding methanol to the precipitate, centrifuging the mixture and collecting the supernatant;
6) Repeating step 5) until the resulting supernatant is colorless;
7) Mixing all the resulting supernatant solutions from steps 4) to 6);
8) Adding 12.5 ml of a 32 wt % hydrochloric acid solution to the resulting mixture from step 7);
9) Centrifuging the resulting suspension and collecting the precipitate;
10) Washing the precipitate with acetone until the supernatant is colorless;
11) Drying the precipitate and dissolving it in water;
12) Dialyzing the resulting solution against a solution of 0.15 M NaCl and 10; to $10^{-5}$ M HCl,
13) Freeze-drying the product.

2. Colouring Method Used in the Examples after Pretreatment and for Reference Swatches Red 4B and Reference Swatch Red 180:

TABLE 1

Comparative Example (EverPlus Red 4B)

| Ingredients | g/l |
|---|---|
| First Composition | |
| PEI-Red 4B | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.05 wt %) |
| Second Composition | |
| Dextran sulfate Sodium salt | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.05 wt %) | pH adjusted to 8 by adding 1.0 mol/l NaOH or 1.0 mol/l HCl

A hair swatch without pretreatment has been coloured according to the following protocol:

(i) Preparing the first and second compositions shortly before application;
(ii) Place hair swatch on plastic wrap or color wraps;
(iii) Work 5 mL of the first composition into the hair tress using a brush;
(iv) Agitating the first composition with the hair swatch for 15 min at 45° C. in a laboratory-type drying cabinet;
(v) Rinsing the hair swatch for 30 s with running lukewarm tap water at a temperature of 30° C. to 35° C.;
(vi) Place hair swatch on plastic wrap or color wraps;
(vii) Work 5 mL of the second composition into the hair tress using a brush;
(viii) Rinsing the hair swatch for 30 s with running lukewarm tap water at a temperature of 30° C. to 35° C.;
(ix) Drying the hair swatch first with tissue paper and then with a hair dryer;
(x) Applying shampoo three times;
(xi) Drying the hair swatch first with tissue paper and then with a hair dryer.

TABLE 2

Comparative Example (Reference Red 180)

| Ingredients | g/l |
|---|---|
| First Composition | |
| PEI-Red 180 | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.05 wt %) |
| Second Composition | |
| Dextran sulfate Sodium salt | 5.00 (0.5 wt %) |
| NaCl | 11.69 (0.2 mol/l) |
| Triethanolamine | 7.46 (0.05 mol/l) |
| Cellosize (TM) hydroxyethyl cellulose QP-4400H, Dow Chemicals | 5.00 (0.05 wt %) | pH adjusted to 8 by adding 1.0 mol/l NaOH or 1.0 mol/l HCl

A hair swatch without pretreatment has been coloured according to the following protocol:

(i) Preparing the first and second compositions shortly before application;
(ii) Place hair swatch on plastic wrap or color wraps;
(iii) Work 5 mL of the first composition into the hair tress using a brush;
(iv) Agitating the first composition with the hair swatch for 15 min at 45° C. in a laboratory-type drying cabinet;
(v) Rinsing the hair swatch for 30 s with running lukewarm tap water at a temperature of 30° C. to 35° C.;
(vi) Place hair swatch on plastic wrap or color wraps;
(vii) Work 5 mL of the second composition into the hair tress using a brush;
(viii) Rinsing the hair swatch for 30 s with running lukewarm tap water at a temperature of 30° C. to 35° C.;
(ix) Drying the hair swatch first with tissue paper and then with a hair dryer;
(x) Applying shampoo three times;
(xi) Drying the hair swatch first with tissue paper and then with a hair dryer.

3. Washing with Shampoo:

Each of the coloured hair swatches which have been obtained in the examples of the present inventions as well as for comparative examples were washed with shampoo 3 times using the following procedure:

(i) Wetting the hair swatch with running tap water for 10 s;
(ii) Adding 0.1 ml shampoo to the hair swatch;
(iii) Rubbing the hair swatch with fingers for 30 s;
(iv) Rinsing the hair swatch with running tap water at a temperature of 30° C. to 35° C. for 30 sec;
(v) Repeating steps (ii) to (iv) 2 more times;
(vi) Drying the hair swatch first with tissue paper and then with a hair dryer.

4. Colour Intensity:

The colour intensity of the pretreated coloured hair swatches obtained in the examples has been compared visually with the colour intensity of a not pretreated coloured hair swatch (reference).

5. Washfastness:

The washfastness of each of the pretreated coloured hair swatches obtained in the examples as well as for comparative example has been evaluated visually comparing the colour intensity of the hair swatch before and after washing the hair swatch with shampoo according to the washing with shampoo procedure.

L*, a*, b* Measurements

The colorimetric parameters in the CIE L* a* b* system have been measured for the hair swatch obtained in selected examples as described in the experimental data.

I. First Set of Experimental Data—Examples of Methods According to the Present Invention Wherein Different Physical Pretreatments have been Used

TABLE 3

| Example 1A: Primer | |
|---|---|
| Ingredients | g/l |
| Cocoamidopropyl Betaine | 10 wt % |

A hair swatch has been pretreated according to the following protocol:
 (i) Priming of swatch for 10 min in MilliQ;
 (ii) Dabbed swatch gently with paper towel;
 (iii) Immersing swatch in pretreatment solution for 1 min and agitating at room temperature;
 (iv) Dabbed swatch gently with paper towel after pretreatment;
 (v) Subsequently colouring swatch as described under 2.

Results and Conclusions:

The ΔE values obtained for Example 1A are summarized in Table 4 below and are compared with the ΔE values obtained for comparative example Red 4B (Example 1A without Primer):

stage 1: initial hair swatch without any treatment
stage 2: pretreated/not pretreated hair swatch with subsequent LbL coating (1 double layer), washed with water
stage 3: pretreated/not pretreated hair swatch with subsequent LbL coating (1 double layer), washed with water, washed with shampoo 3 times

TABLE 4

| Results | | | | |
|---|---|---|---|---|
| Example | Sequence of layers | $\Delta E_{Stage1/Stage2}$[1] | $\Delta E_{Stage1/Stage3}$[2] | $\Delta E_{Stage3/Stage3}$[3] |
| Example 1A | PEI-Red 4B/DxS | 45.2 | 40.1 | 6.6 |
| Reference Red 4B | PEI-Red 4B/DxS | 38.7 | 33.8 | 0.0 |

[1] corresponds to the overall change of colour measured between stage 1 and stage 2 (Color intensity)
[2] corresponds to the overall change of colour measured between stage 1 and stage 3 (Color intensity and Washfastness)
[3] corresponds to the overall change of colour measured between stage 3 (without primer) and stage 3 (with primer) (Increase in Color intensity and Washfastness)

When comparing the ΔE values obtained for comparative example Red 4B and 1A, it can be noticed that $\Delta E_{Stage1/Stage2}$ as well as $\Delta E_{Stage1/Stage3}$ is higher for Example 1A than for comparative example Red 4B. This shows a higher color adsorption is achieved with pretreated hair swatches. This is underlined by comparing the color intensity of comparative example Red 4B with 1A $\Delta E_{Stage3/Stage3}$=6.6. See also the visual comparison in FIG. 1.

TABLE 5

| Example 2A Primer | |
|---|---|
| Ingredients | g/l |
| I) aq. Hydrochloric acid solution, pH 3 | 36.46 (1.0 mol/l) |
| II) aq. Sodium hydroxide solution, pH 10 | 40.0 (1.0 mol/l) |
| III) Ammonium hydroxide solution, pH 10 | 0.25 wt % |

A hair swatch has been pretreated according to the following protocol:
 (i) Immersing swatch in pretreatment solution I, II or III for 10 min and agitating at room temperature;
 (ii) Dabbed swatch gently with paper towel after pretreatment;
 (iii) Subsequently colouring swatch as described under 2.

Results and Conclusions:

The colour intensity of the coloured hair swatches obtained in examples 2AI to 2AII was in the same range as the colour intensity of the coloured hair swatch of comparative example Red 4B or better.

II. Second Set of Experimental Data—Examples of Methods According to the Present Invention Wherein Different Chemical Pretreatments have been Used

TABLE 6

| Example 1B Primer | |
|---|---|
| Ingredients | g/l |
| Hydrogen peroxide solution | 10 wt % | pH adjusted to 8 or 10 by adding 1.0 mol/l NaOH or 1.0 mol/l HCl

A hair swatch has been pretreated according to the following protocol:
 (i) Immersing swatch in pretreatment solution I or II for 10 min and agitating at room temperature;
 (ii) Rinsing the hair swatch with running tap water for 30 sec;
 (iii) Subsequently colouring swatch as described under 2.

Results and Conclusions:
 The ΔE values obtained for Example 1A are summarized in Table 7 below and are compared with the ΔE values obtained for Example 1A without Primer:
 stage 1: initial hair swatch without any treatment (NW)
 stage 2: pretreated/not pretreated hair swatch with subsequent LbL coating (1 double layer), washed with water stage 3: pretreated/not pretreated hair swatch with subsequent LbL coating (1 double layer), washed with water, washed with shampoo 3 times

TABLE 7

| | | Results | | |
|---|---|---|---|---|
| Example | Sequence of layers | $\Delta E_{Stage1/Stage2}$[1] | $\Delta E_{Stage1/Stage3}$[2] | $\Delta E_{Stage3/Stage3}$[3] |
| Example 1B | PEI-Red 4B/DxS | 45.4 | 41.7 | 8.1 |
| Reference Red 4B | PEI-Red 4B/DxS | 38.7 | 33.8 | 0.0 |

[1]corresponds to the overall change of colour measured between stage 1 and stage 2 (Color intensity)
[2]corresponds to the overall change of colour measured between stage 1 and stage 3 (Color intensity and Washfastness)
[3]corresponds to the overall change of colour measured between stage 3 (without primer) and stage 3 (with primer) (Increase in Color intensity and Washfastness)
When comparing the ΔE values obtained for comparative example Red 4B and 1B, it can be noticed that $\Delta E_{Stage1/Stage2}$ as well as $\Delta E_{Stage1/Stage3}$ is higher for Example 1B than for comparative example Red 4B. This shows a higher color adsorption is achieved with pretreated hair swatches. This is underlined by comparing the color intensity of example comparative example Red 4B with 1B $\Delta E_{Stage3/Stage3}$ = 8.1. See also the visual comparison in FIG. 2.

TABLE 8

| Example 2B Primer | |
|---|---|
| Ingredients | g/l |
| Wella Blondor Multiblonde | 200 wt % |
| Wella Welloxon Perfect 6% | 800 wt % |

A hair swatch has been pretreated according to the following protocol:
(i) Priming of swatch for 10 min in MilliQ;
(ii) Dabbed swatch gently with paper towel;
(iii) Brushing swatch with primer composition from each site;
(iv) Agitating swatch for 5 to 15 min and at room temperature;
(iv) Rinsing the hair swatch with running tap water for 2 min;
(v) Subsequently colouring swatch as described under 2.
Results and Conclusions:
The ΔE values obtained for Example 2B are summarized in Table 9 below and are compared with the ΔE values obtained for comparative example Red 4B:
stage 1: initial hair swatch without any treatment
stage 2: pretreated/not pretreated hair swatch with subsequent LbL coating (1 double layer), washed with water
stage 3: pretreated/not pretreated hair swatch with subsequent LbL coating (1 double layer), washed with water, washed with shampoo 3 times

TABLE 9

| | | Results | | |
|---|---|---|---|---|
| Example | Sequence of layers | $\Delta E_{Stage1/Stage2}$[1] | $\Delta E_{Stage1/Stage3}$[2] | $\Delta E_{Stage3/Stage3}$[3] |
| Example 2B | PEI-Red 4B/DxS | 48.1 | 45.7 | 12.2 |
| Reference Red 4B | PEI-Red 4B/DxS | 38.7 | 33.8 | 0.0 |

[1]corresponds to the overall change of colour measured between stage 1 and stage 2 (Color intensity)
[2]corresponds to the overall change of colour measured between stage 1 and stage 3 (Color intensity and Washfastness)
[3]corresponds to the overall change of colour measured between stage 3 (without primer) and stage 3 (with primer) (Increase in Color intensity and Washfastness)

When comparing the ΔE values obtained for comparative example Red 4B and 2B, it can be noticed that $\Delta E_{Stage1/Stage2}$ as well as $\Delta E_{Stage1/Stage3}$ is higher for Example 2B than for comparative example Red 4B. This shows a higher color adsorption is achieved with pretreated hair swatches. This is underlined by comparing the color intensity of comparative example Red 4B with 2B $\Delta E_{Stage3/Stage3}$=12.2. See also the visual comparison in FIG. 3.

TABLE 10

| Example 3B Primer | |
|---|---|
| Ingredients | g/l |
| Ammonium thioglycolate | 6 wt % | pH adjusted to 7.3 by adding 1.0 mol/l NaOH or 1.0 mol/l HCl

A hair swatch has been pretreated according to the following protocol:
(i) Immersing swatch in pretreatment solution for 5 to 10 min and agitating at room temperature;
(ii) Dabbed swatch gently with paper towel;
(iii) Subsequently colouring swatch as described under 2.
Results and Conclusions:
The ΔE values obtained for Example 3B are summarized in Table 11 below and are compared with the ΔE values obtained for Example comparative example Red 4B:
stage 1: initial hair swatch without any treatment
stage 2: pretreated/not pretreated hair swatch with subsequent LbL coating (1 double layer), washed with water
stage 3: pretreated/not pretreated hair swatch with subsequent LbL coating (1 double layer), washed with water, washed with shampoo 3 times

TABLE 11

| | | Results | | |
|---|---|---|---|---|
| Example | Sequence of layers | $\Delta E_{Stage1/Stage2}$[1] | $\Delta E_{Stage1/Stage3}$[2] | $\Delta E_{Stage3/Stage3}$[3] |
| Example 3B | PEI-Red 4B/DxS | 53.5 | 47.6 | 9.7 |
| Reference Red 180 | PEI-Red 4B/DxS | 38.7 | 33.8 | 0.0 |

[1] corresponds to the overall change of colour measured between stage 1 and stage 2 (Color intensity)
[2] corresponds to the overall change of colour measured between stage 1 and stage 3 (Color intensity and Washfastness)
[3] corresponds to the overall change of colour measured between stage 3 (without primer) and stage 3 (with primer) (Increase in Color intensity and Washfastness)

When comparing the ΔE values obtained for comparative example Reference Red 180 and 3B, it can be noticed that $\Delta E_{Stage1/Stage2}$ as well as $\Delta E_{Stage1/Stage3}$ is higher for Example 3B for 5 as well as 10 min than for comparative example Reference Red 180. This shows a much higher color adsorption is achieved with pretreated hair swatches. This is underlined by comparing the color intensity of comparative example Reference Red 180 with 3B $\Delta E_{Stage3/Stage3}$=9.7 for 5 min priming and 15.0 for 10 min priming, respectively. See also the visual comparison in FIG. 4.

TABLE 12

| Example 4B Primer | |
|---|---|
| Ingredients | g/l |
| Sodium hypochlortet | 1 wt % |

A hair swatch has been pretreated according to the following protocol:
(i) Immersing swatch in pretreatment solution for 5 to 10 min and agitating at room temperature;
(ii) Rinsing the hair swatch with running tap water for 30 sec;
(iii) Subsequently colouring swatch as described under 2.

Results and Conclusions:
The ΔE values obtained for Example 4B are summarized in Table 13 below and are compared with the ΔE values obtained for comparative example Reference Red 180 without Primer:
stage 1: initial hair swatch without any treatment
stage 2: pretreated/not pretreated hair swatch with subsequent LbL coating (1 double layer), washed with water
stage 3: pretreated/not pretreated hair swatch with subsequent LbL coating (1 double layer), washed with water, washed with shampoo 3 times When comparing the ΔE values obtained for comparative example Reference Red 180 and 4B, it can be noticed that $\Delta E_{Stage1/Stage2}$ as well as $\Delta E_{Stage1/Stage3}$ is higher for Example 4B for 5 as well as 10 min than for comparative example Reference Red 180. This shows a much higher color adsorption is achieved with pretreated hair swatches. This is underlined by comparing the color intensity of comparative example Reference Red 180 with 4B $\Delta E_{Stage3/Stage3}$=9.7 for 5 min priming and 15.0 for 10 min priming, respectively. See also the visual comparison in FIG. 5.

III. Third Set of Experimental Data—Examples of Methods According to the Present Invention Wherein Polymeric Pretreatments have been Used Example 1C A hair swatch was pretreated according to the following protocol:
(i) Priming of swatch for 10 min in MilliQ;
(ii) Dabbed swatch gently with paper towel;
(iii) Brushing swatch with a first primer composition comprising a cationic polymer (PEI) from each site;
(iv) Agitating swatch for 5 to 15 min and at room temperature;
(v) Rinsing the hair swatch with running tap water for 2 min;
(vi) Priming of swatch for 10 min in MilliQ;
(vii) Dabbed swatch gently with paper towel;
(viii) Brushing swatch with a second primer composition comprising an anionic polymer (DxS) from each site;
(ix) Agitating swatch for 5 to 15 min and at room temperature;
(x) Rinsing the hair swatch with running tap water for 2 min;
(xi) Repeating steps (i) to (x),
(xii) Subsequently colouring swatch according to step c1) of the present invention with a first composition com-

TABLE 13

| | | Results | | |
|---|---|---|---|---|
| Example | Sequence of layers | $\Delta E_{Stage1/Stage2}$[1] | $\Delta E_{Stage1/Stage3}$[2] | $\Delta E_{Stage3/Stage3}$[3] |
| Example 4B | PEI-Red 4B/DxS | 55.1 | 54.8 | 11.4 |
| Reference Red180 | PEI-Red180/DxS | 38.7 | 33.8 | 0.0 |

[1] corresponds to the overall change of colour measured between stage 1 and stage 2 (Color intensity)
[2] corresponds to the overall change of colour measured between stage 1 and stage 3 (Color intensity and Washfastness)
[3] corresponds to the overall change of colour measured between stage 3 (without primer) and stage 3 (with primer) (Increase in Color intensity and Washfastness)

prising a cationic polymer (PEI) and a second composition comprising an anionic polymer (DxS).

Reference Example 1C

A swatch was coloured according to step c1) of the present invention with a first composition comprising a cationic polymer (PEI) and a second composition comprising an anionic polymer (DxS) without polymer preatreatment.
Results:
The ΔE value obtained for Example 1C compared to Reference Example 1C was 7.4.

Example 2C

For Example 2C, Example 1C was repeated with the only difference that Polystyrene sulfonate (PSS) was used as anionic polymer in the second primer composition instead of DxS.

Reference Example 2C

For Reference Example 2C, Reference Example 1C was repeated with the only difference that Polystyrene sulfonate (PSS) was used as anionic polymer in the second composition instead of DxS.
Results:
The ΔE value obtained for Example 2C compared to Reference Example 2C was 4.3.

Example 3C

For Example 3C, Example 2C was repeated with the only difference that step (xi) was not carried out.

Reference Example 3C

Reference Example 3 corresponds to Reference Example 2.
Results:
The ΔE value obtained for Example 1C compared to Reference Example 3C was 4.5. The results show that an improvement of the colouration can be obtained when treating the hair with a first primer composition comprising cationic polymers and a second primer composition comprising anionic polymers, or even when repeating any of these steps.

Combinations

A. A method for colouring hair comprising:
   carrying out the following sequence of steps:
      a) pretreating a first portion of the hair with at least one primer composition to modify the surface of the hair,
      b) optionally repeating step a) at least once;
      c) treating a second portion of the hair with a hair colouring system comprising at least one cationic polymer and/or at least one anionic polymer,
   wherein the first and second portions of the hair have at least one common area.
B. The method according to paragraph 1, wherein the primer composition comprises at least one of
   an oxidizing agent, such as a peroxide,
   a reducing agent,
   a pH>9,
   a salt such as a cosmetically acceptable salt,
   a surfactant,
   an oil, and
   an organic acid.
C. The method according to any of the preceding paragraphs, wherein modifying the surface of the hair includes modifying the overall negative charge of the hair surface, such as increasing the overall negative charge of the hair surface.
D. The method according to any one of preceding paragraphs, wherein the primer composition comprises a surfactant selected from the group consisting of a cationic surfactant, anionic surfactant, non-ionic surfactant and amphoteric surfactant, and combinations thereof.
E. The method according to paragraph D, wherein the amphoteric surfactant is selected from the group consisting of betain, sultaines, phospholipids, aminopropionates, aminoglycinates, amphoacetate, amphodiacetate, amphopropionate, amphohydroxypropylsulfonates and combinations thereof.
F. The method according to any one of preceding paragraphs, wherein the primer composition comprises an oxidizing agent, such as a peroxide, optionally in an amount ranging from 0.1% to 12%, alternatively from 1% to 7%, alternatively from 2% to 5%, by total weight of the primer composition.
G. The method according to any one of preceding paragraphs, wherein the primer composition comprises a reducing agent.
H. The method according to any of the preceding paragraphs, wherein the primer composition does not comprise at least one of a dye and polymer, particularly is substantially free of cationic polymer.
I. The method according to any of the preceding paragraphs, wherein step a) comprises pretreating the first portion of the hair with a first primer composition, and step b) comprises pretreating the first portion of the hair with a second primer composition which is different from the first primer composition.
J. The method according to paragraph I, wherein the first primer composition comprises at least one anionic surfactant, and is optionally substantially free of cationic polymers and cationic surfactants.
K. The method according to paragraph I, wherein the first primer composition comprises an uncoloured cationic polymer and the second primer composition comprises an uncoloured anionic polymer.
L. The method according to any of the preceding paragraphs, wherein step c) comprises
   c1) carrying out the following sequence of steps:
      i) applying a first composition comprising the cationic polymer to a third portion of the hair; and
      ii) applying a second composition comprising at least one anionic polymer to a fourth portion of the hair;
   the third and fourth portions of the hair having the second portion of the hair as common area, and optionally
   c2) repeating step c1) at least once, wherein the common area of each of the repeated steps c1) has at least one common area with:
      the common area of the first and second portions,
      the common area of each of the other repeated steps c1) in case step c1) is repeated more than once.

M. The method according to any of the preceding paragraphs, wherein the cationic polymer is selected from the group consisting of linear polyethyleneimine, branched polyethyleneimine, polyallylamine hydrochloride, polydiallyldimethylammonium chloride, copolymers thereof and mixtures thereof.

N. The method according to any one of paragraphs L to M, wherein in step c1) and/or in at least one of the repeated steps c1), the cationic polymer is a coloured cationic polymer.

O. The method according to any one of paragraphs L to N, wherein the anionic polymer is selected from the group consisting of polystyrene sulfonate salts, λ-Carrageenan, Dextran sulfate salts, polyacrylic acid, poly (methacrylic acid) salts, alginic acid salts, carboxymethylcellulose salts, copolymers thereof and mixtures thereof.

P. A hair colouration obtainable by the method according to any one of preceding paragraphs.

Q. A kit for colouring hair comprising a first compartment comprising the primer composition as defined in any one of the preceding claims and a second compartment comprising the hair colouring system as defined in any one of the preceding claims.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for colouring hair comprising:
carrying out the following sequence of steps:
a) in advance of coloring the hair, pretreating the hair with at least one non-polymeric primer composition to form modified hair, wherein the non-polymer primer composition comprises an oxidizing agent in combination with a pH of at least 9 and a surfactant, and the non-polymer primer composition does not comprise a dyestuff, a chromophore, a fluorophore, an oxidative dye primary developer, an oxidative dye coupler or a direct dye,
b) optionally repeating step a) at least once,
c) treating the modified hair with a hair colouring system comprising a first composition having a pH of from 7 to 9 and at least one cationic polymer having at least one covalently bonded pendant and/or in-chain chromophore and/or fluorophore to form a cationic polymer layer on the modified hair,
d) overlaying the layer of cationic polymer on the modified hair with a second composition having a pH of from 5 to 6 and at least one anionic polymer optionally having at least one covalently bonded pendant and/or in-chain chromophore and/or fluorophore to form a dual polymeric layer on the modified hair.

2. The method according to claim 1, wherein the surfactant is selected from the group consisting of a cationic surfactant, anionic surfactant, non-ionic surfactant and amphoteric surfactant, and combinations thereof.

3. The method according to claim 2, wherein the surfactant is an the amphoteric surfactant selected from the group consisting of betain, sultaines, phospholipids, aminopropionates, aminoglycinates, amphoacetate, amphodiacetate, amphopropionate, amphohydroxypropylsulfonates and combinations thereof.

4. The method according to claim 1, wherein the oxidizing agent is present in an amount ranging from 0.1% to 12% by total weight of the primer composition.

5. The method according to claim 1, wherein step a) comprises pretreating the hair with a first primer composition which comprises the non-polymer composition in which the surfactant is at least one anionic surfactant and is substantially free of cationic polymers and cationic surfactants, and step b) is carried out and further comprises pretreating the hair with a second primer composition which comprises the non-polymer composition in which the surfactant is a cationic surfactant.

6. The method according to claim 1, wherein the cationic polymer is selected from the group consisting of linear polyethyleneimine, branched polyethyleneimine, polyallylamine hydrochloride, polydiallyldimethylammonium chloride, copolymers thereof and mixtures thereof.

7. The method according to claim 1, wherein the anionic polymer is selected from the group consisting of polystyrene sulfonate salts, λ-Carrageenan, Dextran sulfate salts, polyacrylic acid, poly(methacrylic acid) salts, alginic acid salts, carboxymethylcellulose salts, copolymers thereof and mixtures thereof.

* * * * *